United States Patent [19]

Farrar et al.

[11] Patent Number: 4,662,358
[45] Date of Patent: May 5, 1987

[54] ELECTRONIC CONTROL SYSTEM FOR A CARDIAC PROSTHESIS

[75] Inventors: David J. Farrar, Richmond; Thomas C. Robinson, Berkeley, both of Calif.

[73] Assignee: Thoratec Laboratories Corporation, Berkeley, Calif.

[21] Appl. No.: 601,257

[22] Filed: Apr. 17, 1984

[51] Int. Cl.$^4$ ............................................. A61B 19/00
[52] U.S. Cl. ........................................ 128/1 D; 623/3
[58] Field of Search ............................ 128/1 D; 623/3

[56] References Cited

U.S. PATENT DOCUMENTS 3,783,453  1/1974  Bolie ........................................ 623/3
3,966,358  6/1976  Heimes et al. ........................... 623/3
4,231,354  11/1980  Kurtz et al. ............................ 623/3

OTHER PUBLICATIONS

V. I. Shumakov et al., *Maintenance of the Circulation In Vivo by an Implanted Automatically Controlled Artificial Heart*, Plenum Publishing Corporation (1973).
T. K. Oh et al., *Automatic Control of the Artificial Heart*, Abstract, 4th ESAO, Nov. 1977.
W. S. Pierce, et al., *Automatic Control of the Artificial Heart*, Trans. Amer. Soc. Artif. Int. Organs, vol. XXII, 1976, pp. 347-355.
B. Vajapeyam et al., *A Microcomputer Based Control System for the Artificial Heart*, Trans. Am. Soc. Artif. Intern. Organs, vol. XXV, 1979, pp. 379-382.
Y. Mitamura, *An Optical Volume Sensor for Control and Monitoring of a Pneumatic Assist Pump*, Am. Soc. Artif. Intern. Organs, p. 8.
H. Takagi, *Automatic Control of the Artificial Heart with the Precise Response to the Venous Return*, Abstract, p. 13.
Peter M. Newgard et al., *Implantable Electrical Power and Control System for Artificial Hearts*, pp. 799-805.
M. Arabia et al., *A New Automatically Controlled Electric TAH*, Trans. Am. Soc. Artif. Intern. Organs, vol. XXVI, 1980, pp. 60-65.
V. I. Shumakov et al., *Control System for an Artificial Heart*, Plenum Publishing Corporation, 1979, pp. 190-195.
A. K. Vakamudi et al., *Control Systems for the Total Artificial Heart*, pp. 372-381.
F. M. Donovan, Jr., *Artificial Heart Controls Supoort*, U.S. Atomic Energy Commission, Aug. 1, 1973-Jul. 31, 1974.

(List continued on next page.)

Primary Examiner—Kyle L. Howell
Assistant Examiner—Ruth S. Smith
Attorney, Agent, or Firm—Banner, Birch, McKie & Beckett

[57] ABSTRACT

An electronic control system for controlling the operation of a cardiac prosthesis is disclosed. The cardiac prosthesis includes dominant and subordinate ventricles which receive blood in response to body requirements and an actuation device coupled to the ventricles for ejecting blood from the ventricles. The electronic control system includes sensing devices to determine the volume of blood in the ventricles as a function of time. A control device, which in the preferred embodiment is a programmed microcomputer, includes a clock controller which first determines the filling flow rates of the ventricles from the volume information from the sensing devices. The ventricle with the greatest filling flow rate is selected as the dominant ventricle. The clock controller then adjusts the heart rate of the cardiac prosthesis as a function of the filling flow rate of the dominant ventricle to allow just enough time for the dominant ventricle to fill completely. The control device further includes first and second ejection rate controllers which generate control signals to adjust the ejection rates of the dominant and subordinate ventricles in accordance with adjusted heart rate so the dominant and subordinate ventricles can eject all blood in the time allowed by the adjusted heart rate. The control signals are supplied to pump motors to contro the operation of pump motors which in turn drive the actuation device to eject blood from the ventricles.

41 Claims, 13 Drawing Figures

OTHER PUBLICATIONS
(SEE TOP SHEET)

M. P. duPlessis et al., *In-Vitro and Predicted In-Vitro Performance of a Pneumatically Regulated Artificial Ventricle*, Journal of Biomechanical Engineering, May 1977, pp. 83–90.

F. Klimes, et al., *Analysis and Model of Controlling System to Control Heart Rate and Stroke Volumes of an Artificial Heart*, Medical and Biological Engineering, Sep. 1975, pp. 662–668.

W. S. Pierce et al., *Portable Artificial Heart Systems*, Trans. Am. Soc. Artif. Intern. Organs, 1983, pp. 745–759.

Tadayoshi Hongo, M.D. et al., *Introduction of New Improved Pumping Modes in the Total Artificial Heart (TAH)*, Cardiovascular Diseases, Bulletin of the Texas Heart Institute, vol. 4, No. 3, pp. 323–334.

T. H. Stanley et al., *Metabolic Monitoring and Control of the Artificial Heart*, 26th ACEMB, Sep. 20–Oct. 4, 1973, p. 281.

E. Henning et al., *The Relationship of Cardiac Output and Venous Pressure in Long Surviving Calves with Total Artificial Heart*, Trans. Am. Soc. Artif. Intern. Organs, vol. XXIV, 1978, pp. 616–620.

Akira Kamiya et al., *Effects of Unphysiological Factors on Cardiac Output Regulation During Artificial Heart Pumping*, IEEE Transactions on Biomedical Engineering, vol. BME-22, No. 3, May 1975, pp. 238–245.

Ashok K. Vakamudi et al., *Quantifying Stroke Volume and Cardiac Output in Total Artificial Hearts*, Journal of Clinical Engineering, vol. 4, No. 1, Jan.–Mar. 1979, pp. 45–48.

Kirby W. Hiller et al., *Mechanism to Drive an Artificial Heart Inside the Chest*, Trans. Am. Soc. Artif. Intern. Organs, vol. 8 (1962).

Kirby W. Hiller et al., *An Electronic-Mechanical Control for an Intrathoracic Artificial Heart*, The American Journal of Medical Electronics, pp. 212–221.

Setsuo Takatani et al., *Pusher-Plate Type TAH System Operated in the Left and Right Free-Running Variable Rate Mode*, International Society for Artificial Organs, vol. 5, No. 2, pp. 132–142.

J. H. Kennedy et al., *The Impact of Artificial Heart Devices on Cardiovascular Control*, Transplantation Proceedings, vol. VI, No. 3, Supplement 1 (Sep., 1974, pp. 49–59.

Lawrence K. Altman, *Heart Team Sees Lessons in Dr. Clark's Experience*, New York Times (4/17/83).

William S. Pierce, M.D. et al., *The Artificial Heart*, Arch Surg.—vol. 112, Dec. 1977, pp. 1430–1438.

Kou Imachi et al., *System Analysis on Control Softwares and Haemodynamic Studies of Total Artificial Heart Utilizing Simulation Model*, Institute of Medical Electronics, pp. 122–125.

D. L. Landis et al., *Long-Term In Vivo Automatic Electronic Control of the Artificial Heart*, Trans. Am. Soc. Artif. Intern. Organs, vol. XXIII, 1977, pp. 519–525.

L. R. Golding et al., *Chronic Nonpulsatile Blood Flow*, Trans. Am. Soc. Artif. Intern. Organs, vol. XXVII, 1982, pp. 81–85.

N. N. Puri et al., *Control System for Circulatory Assist Devices: Dertmination of Suitable Control Variables*, Trans. Am. Soc. Artif. Intern. Organs, vol XXVIII, 1982, pp. 127–132.

S. Takatani et al., *Optimum Control Mode for a Total Artificial Heart*, Trans. Am. Soc. Artif. Intern. Organs, vol. XXVIII, 1982, pp. 148–153.

S. Kimura et al., *Development of Long-Term Circulatory Assist Device, Possessing Servomatic Flow Regulation System Stabilizing Venous Return Cardiac Output Imbalance*, Trans. Am. Soc. Artif. Intern. Organs, vol. XXVIII, 1982, pp. 169–172.

R. Schistek et al., *Total Implantable Axial Nonpulsatile Blood Pump for Left Ventricular Assist and Total Artificial Heart Replacement*, Trans. Am. Soc. Artif. Intern. Organs, vol. XXVII, 1982, pp. 589–593.

L. Brownstein et al., *Operation of Cardiopulmonary Bypass Versus an Intracorporeal Total Artificial Heart*, Trans. Am. Soc. Artif. Intern. Organs, vol. XXIX, 1983, pp. 110–115.

S. D. Nielsen et al., *Noninvasive Cardiac Monitoring and Diagnostics for Pneumatic Pumping Ventricles*, Trans. Am. Soc. Artif. Intern. Organs, vol. XXIX, 1983, pp. 589–592.

H. Reul et al., *A Hydraulic Analog of the Systemic and Pulmonary Ciculation for Testing Artificial Hearts*, ESAO II, pp. 120–127.

ELECTRONIC CONTROL SYSTEM FOR A CARDIAC PROSTHESIS

CROSS-REFERENCE TO RELATED APPLICATIONS

This application is related to two previously filed U.S. Pat. Nos. 4,369,530 and 4,376,312, both filed on May 19, 1981, and now U.S. Pat. Nos. 4,369,530 and 4,376,312, respectively. The inventors of the first of these applications are Thomas J. Robinson and Sotiris Kitrilakis, and the inventors of the second application are the above inventors and Thomas B. Martin, Jr. These applications, which are direction to an "Hydraulically Actuated Cardiac Prosthesis," are incorporated by reference in the specification of the present application.

BACKGROUND OF THE INVENTION

This invention relates to the field of cardiac prosthetic devices and, more particularly, to an electronic control system for an artificial heart and circulatory assist device, especially for use by and implantation in humans.

It has been estimated that between 16,000 and 50,000 patients annually are suitable candidates for implantation of a total cardiac prosthesis (TCP). Such candidates typically are disabled due to insufficient left and right ventricular function, but are otherwise in good health. Many thousands more annually, having inadequate left ventricular function and satisfactory right ventricular function, may be candidates for a permanently implanted left ventricular assist device (LVAD).

The ideal total cardiac prosthesis must provide complete rehabilitation for the patient. Such a TCP recipient must be able to engage in gainful employment and all normal activities, including moderate exercise. He should retain a substantially normal appearance and normal or near normal mobility with no significant limitations of any kind. Cardiac output effected by the TCP must be normal, adequat and sufficiently responsive to the patient's requirements to accommodate expected, sudden changes in physical activity or emotional stress level. The presence and operation of the TCP must be sufficiently unobtrusive so that the patient can largely forget that he is dependent on an artificial heart. All blood pumping functions of the TCP should be completely automatic, so that the patient performs no control or monitoring functions except for maintaining adequate power to the TCP and responding to warnings that indicate a lack of power or serious problems requiring immediate technical or medical attention.

The intrathoracic blood pumping components of the TCP must be similar in size and weight to the natural heart. TCP life must be sufficiently long and reliability sufficiently high that risk to the patient of sudden prosthesis failure and its attendant anxiety are minimized. The formation of pannus and adherent thrombus must be prevented to avoid a compromise of blood pump function. Thrombo-emboli and excessive blood damage also must be prevented. The TCP must not damage adjacent tissues or impair organ function by toxicity and adverse tissue reactions, by mechanical trauma or compression, or by excessive local temperatures. The system must avoid skin penetrations of any kind to prevent infections that can arise from percutaneous leads. This eliminates a major risk to the patient, reduces the need for clinical observation and treatment, and reduces the maintenance of the TCP required of the patient. This ideal system must be low in cost to purchase, implant and maintain. The frequency and extent of routine monitoring and maintenance, both medical and technical, must be low.

Serious research toward the realization of a total cardiac prosthesis has been under way since about 1957, sponsored largely by the U.S. National Institute of Health (NIH). Researchers have directed this research to six principal areas: (1) blood-compatible materials for the blood pumping device; (2) heart valves; (3) blood pumps; (4) blood pump actuating devices; (5) power supplies and their application to the internal blood pump actuating device; and (6) control mechanisms for the pumping function.

The prior related applications Ser. No. 265,100 and Ser. No. 265,199 discuss previous research and development in blood-compatible materials, heart valves, blood pumps and blood pump actuating devices. The discussion in these applications is hereby incorporated by reference in this application. In addition, these prior related applications are principally directed to an hydraulically actuated blood pump and blood pump actuating device. This hydraulically actuated system includes an actuation fluid reservoir, an actuation fluid pump in fluid communication with the reservoir for providing intermittent pulses of actuation fluid and an actuation chamber having an actuation fluid inlet path in fluid communication with the pump and a separate actuation fluid outlet path in fluid communication with the reservoir. The actuation chamber causes displacement of a flexible portion or bladder of a blood pumping chamber in response to changes in the volume of actuation fluid in the actuation chamber. The hydraulically actuated system also includes a valve associated with the actuation chamber to close or open the actuation fluid outlet ath primarily in response to forces which vary as a function of actuation fluid flow through the actuation fluid inlet path. The operation of the valve, the actuation fluid pump and the actuation chamber expels blood from the blood pumping chamber after the blood pumping chamber fills with blood. Thus, these prior related applications disclose a practical blood pump actuating mechanism which, for the sake of convenience, is incorporated in this application.

On the subject of power, up to this time, most TCPs implanted in calves have been powered pneumatically via transcutaneous tubing into the thoracic cavity. A large external console supplies the proper regimen of pressure variations in order to activate the internal blood pump. With such a system, calves have lived up to 221 days (Jarvik, "The Total Artificial Heart," *Scientific American*, Vol. 244, No. 1, pp. 74-80, January, 1981). On another tack, NIH has sponsored considerable effort on the development of internal nuclear power supplies and, to a lesser extent, of chemical fuel cells. None of this work, however, appears to be promising; in fact, the nuclear effort was terminated by the U.S. Energy Research and Development Administration. Additionally, various means of transmitting mechanical power transcutaneously have been attempted, but none appears to be promising. At present, transcutaneous transmission of electricity appears to be the preferred method for powering a TCP. A second, less preferable possibility is the supplying of electrical power through percutaneous wire penetrations, but these always pose a threat of infection and are psychologically annoying to the patient.

Several investigators have developed the technique of transcutaneous electrical transmission. Their approach is to implant a coil under the skin. This coil functions as a transformer secondary winding, receiving power from an inductively coupled, external mating coil juxtaposed therewith to serve as the transformer primary winding. At frequencies on the order of 17 kHz, up to 100 watts of power have been transmitted for many months across the skin of a dog. See J. C. Schuder et al, "Ultra High Power Electromagnetic Energy Transport Into the Body," *Trans. ASAIO,* 1971, incorporated herein by reference. Thus, the inductive delivery across the intact skin of approximately 30 watts of power to a TCP appears to be well within the state of the art.

On the subject of control of a TCP to make it sympathetic to the body, there have been many different approaches and much controversy. Some researchers have attempted to provide no active control, while others have required control in order to achieve regular beating. See, e.g., W. H. Burns et al, "The Total Mechanical Cardiac Substitute," *Process in Cardiovascular Diseases,* Vol. XII, No. 3, 1969, pp. 302-311. Some systems have attempted to control systole (i.e., the contraction phase of the cardiac cycle whose rate is one determinant of cardiac output) from the left ventricle of the TCP in order to control the systolic pressure in the aorta. Still other systems have attempted feedback control of stroke volume and beat rate.

The natural heart and at least some, if not all, TCPs are comprised of two pumps in series. The right pump or ventricle receives blood from the vena cava and ejects it into the pulmonary artery. The left pump or ventricle receives blood from the pulmonary veins and ejects blood into the systemic circulatory system via the aorta. Over a time period considerably longer than that of a few beats, the left pump will pump more blood than the right pump. To prevent an imbalance of blood volume, a deficiency or excess of blood pumped by the right and left ventricles must be avoided. Various investigators have included controls in their TCP systems in order to achieve the critical balance between the pumping rate of the right and left ventricles. The major intrinsic mechanism by which the natural heart controls cardiac output is described by Starling's law of the heart, which essentially states that the output during systole is proportional to the amount of blood which flows into the relaxed ventricle during diastole. The body controls peripheral vascular resistance and venous "tone" according to the needs of the body's organs so that blood flowing to, and venous return from, the body is increased when there is a demand for higher blood flow. This increased return is accompanied by increases in venous and atrial filling pressures normally ranging from 0 to 10 mm Hg, which drives blood from the vena cava through the tricuspid valve into the relaxed right ventricle during diastole.

Similarly, for the left ventricle, the pressure in the pulmonary veins and left strium normally varies from 5 to 15 mm Hg and is proportional to venous return from the pulmonary vascular network into the left ventricle. If the right ventricle should temporarily pump slightly more than the left ventricle, the pressure rises in the pulmonary artery and, as a consequence, in the pulmonary veins, causing more blood to flow into the left ventricle and thereby matching the pumping output of the left ventricle to that of the right ventricle. Thus, the natural heart achieves the necessary balance between the two pumps in series via simple and direct fluid dynamic means. In a real sense, the heart is the servant, not the master of the circulatory system. It is basically just a pump which must respond to the requirements of the body by pumping precisely that which returns to it. The above-described intrinsic control can maintain body function even in the absence of extrinsic humoral or neural control.

The body also neurally controls the rate at which the natural heart beats. Cardiac output is a function of the amount of blood ejected during systole, and the rate at which the heart beats. For all but the most strenuous activity, the systolic stroke volume per beat remains substantially constant. Thus, cardiac output is primarily a function substantially constant. Thus, cardiac output is primarily a function of heart rate (i.e., the number of beats per minute). Heart rates can vary from a low of about 40 to as high as 220 beats per minute in a young person, and ordinarily from about 60 to 150 bpm in an adult. Cardiac output of the natural heart can vary from about 4 to as high as 24 liters per minute, the latter being the case of a trained athlete. Experience with transplanted natural hearts shows that direct neural control is unnecessary for a satisfactory life. However, transplanted hearts do respond indirectly to neural commands since the peripheral vascular system and venous return to the heart are regulated by the nervous system.

The natural control system also regulates arterial blood pressure in order to maintain adequate circulation to the vital organs. The mean arterial pressure is established by cardiac output and the peripheral resistance of the vascular systems. In some of the TCPs which previously have been developed, a control means has been provided to maintain pressure in the aorta and atrium within a reasonable range. Pierce et al, "Automatic Control of the Artificial Heart," *Trans. Amer. Soc. Artif. Int. Organs,* Vol. II, pp. 347-356 (1976); Kirby W. Hiller et al, "An Electronic-Mechanical Control for an Intrathoracic Artificial Heart," *American Journal of Medical Electronics,* July-September of 1963, pp. 212-221; Hiller et al, "Mechanism to Drive An Artificial Heart Inside the Chest." pp. 125-130 (1962); B. Vajapeyam, "A Microcomputer Based Control System for the Artificial Heart," *Trans. ASAIO,* Vol. XXV, pp. 379-382 (1979); M. Arobia et al, "A New Automatically Controlled Electric TAH," *Trans. ASAIO,* Vol. XXVI, pp. 60-65 (1980); V. I. Shumakeov et al, "Control System for an Artificial Heart," translated from *Meditsinskaya Tekhnika,* No. 4, pp. 22-29 (July-August), Plenum Publishing Co.; F. Klines et al, "Analysis and Model for Controlling System to Control Heart Rate and Stroke Volumes of an Aritficial Heart," *Medical and Biological Engineering, pp.* 662-668, September 1975. On the other hand, there is evidence from natural heart transplants that such control is unnecessary; transplanted human hearts have no neural connections to the host body, and hence their cardiac output is only indirectly related to neural control; yet people with such transplants have been able to lead meaningful lives. It may be concluded that a TCP can be satisfactorily operated without such control. The evidence above teaches that a workable TCP can be made to approximate the natural heart's Starling's Law behavior with relatively simple control operations.

Thus, a TCP is now technically feasible, provided that a competent design is constructed. The critical blood pumping technology appears to be established and adequate for long-term survival of the recipient. Benign power transmission across the skin can obviate the portent of infection of the thoracic cavity transmitted via percutaneous leads. One major area where satisfactory progress has recently been made is in the development of a blood pump and blood pump actuating mechanism as set forth in the prior related Pat. Nos. 4,369,530 and 4,376,312. Another major area where satisfactory progress has been lacking, however, is the provision of a reliable and effective electronic control system for a TCP. This latter objective is the one to which the present invention is principally addressed.

SUMMARY OF THE INVENTION

Accordingly, it is an object of the present invention to provide a control system for a cardiac prosthesis and circulatory assist device which obviates many of the drawbacks of the prior art electronic control systems.

In particular, it is an object of the present invention to provide a simple and reliable electronic control system for a cardiac prosthesis which obeys Starling's law by generating control signals to cause cardiac output to equal venous return.

It is also an object of the present invention to provide a control system which allows the dominant ventricle, i.e., the ventricle with the greatest filling flow rate, of a TCP to fill completely with blood and adjusts the heart rate accordingly so the end diastolic volume of the dominant ventricle equals maximum ventricular volume.

It is a further object of the present invention to provide an electronic control system for a cardiac prosthesis which changes the heart rate and the ejection rates of the left and right ventricles in response to detection of the volume of blood in the blood pump.

Another object of the present invention is to provide an electronic control system for a cardiac prosthesis which is compact, reliable, and has a long life. More specifically, it is an object of the present invention to provide an electronic control system which uses microprocessing technology to control the operation of the TCP.

Another object of the invention is to provide a total cardiac prosthesis which is substantially unobtrusive and permits the patient to engage in all normal activities, without significant limitations of any kind.

Another object of the invention is to provide a total cardiac prosthesis wherein all blood pumping functions are completely automatic, and wherein minimum patient attention is required to maintain prosthesis operation.

Another object of the invention is to provide a total cardiac prosthesis which permits monitoring of mechanical and physiological information, and which is provided with alarms to warn of power failures or other malfunctions.

Another object of the present invention is to provide an electronic control system which relies upon a transcutaneous power supply system for inductively transmitting power from an external wearable component to the internal electronic control system.

These and other objects of the present invention are accomplished in the most basic form of this invention by providing an electronic control system which controls an actuation system for supplying motive power to a blood pumping chamber. The electronic control system is responsive to the volume of blood in the blood pumping chamber to control the actuation system so that cardiac output can be adjusted to equal venous return (Starling's law). In particular, the electronic control system includes a clock controller which adjusts the clock time or heart rate of the blood pumping chamber so the blood pumping chamber is allowed just enough time to fill to the desired level, preferably completely. The electronic control system further includes an ejection rate controller, which receives the adjusted clock time or heart rate from the clock controller and also receives volume signals from the blood pumping chamber, to adjust the ejection rate of the blood pumping chamber by generating control signals. These control signals control the operation of a pump motor which is part of the actuation system. The ejection rate of the blood pumping chamber is adjusted so the blood pumping chamber ideally can eject all the blood in the chamber within the time period allowed by the adjusted clock time or heart rate. In this preferred manner, the end diastolic volume of the blood pumping chamber equals the maximum ventricular volume and cardiac output equals venous return, i.e., the blood pumping chamber obeys Starling's law.

In the total cardiac prosthesis of the present invention, there are two blood pumping chambers, i.e., a left ventricle and a right ventricle. The ventricle which has the greatest filling flow rate, normally the left ventricle, is made the dominant ventricle. The clock controller of the electronic control system adjusts the clock time so that the dominant ventricle is always allowed just enough time to fill to the desired level, preferably completely. A left ventricle ejection rate controller then controls the left ventricle ejection rate as described above. Similarly, a right ventricle ejection rate controller is provided as part of the electronic control system for adjusting the ejection rate of the right ventricle in accordance with the adjusted clock time and volume signals from the right ventricle. The ejection rates determined by the right and left ejection rate controllers of the electronic control system ideally are set so that Starling's law is obeyed, i.e., cardiac output is made equal to venous return. Thus, the TCP of the present invention is completely responsive to the demands of the body.

The present invention also is directed to an implantable electronic control system for controlling a blood pumping system in which the electronic control system is controlled by a programmed microprocessing system. The programmed microprocessing system is responsive to signals proportional to blood volume generated by a sensing device associated with the dominant ventricle to adjust the clock rate or heart rate of the blood pumping system. The microprocessing system allows the dominant ventricle just enough time to fill completely and adjusts the heart rate accordingly. The microprocessing system also adjusts the ejection rate of the dominant ventricle in accordance with the adjusted clock rate and the volume-dependent signals from the dominant ventricle. The microprocessing system operates the dominant and subordinate ventricles alternately, so that the subordinate ventricle partially fills with blood during its portion of the operation cycle. The microprocessing system also adjusts the ejection rate of the subordinate ventricle to eject all the blood contained therein within the portion of time allotted to the subordinate ventricle, as determined by the adjusted heart rate. Thus, the microprocessor-controlled electronic control system of the present invention is a fully automatic system which is responsive to the instantaneous volume of blood in the ventricles to adjust the operation of the hydraulically actuated blood pumping system so that cardiac output equals venous return.

The present invention also includes a method of operating a total cardiac prosthesis (TCP) and an electronic control system for the cardiac prosthesis. The method includes the steps of adjusting the clock time or heart rate of the TCP in response to the volume signals received by the electronic control system from the dominant ventricle. The heart rate is adjusted so the dominant ventricle has just enough time to fill preferably completely. The method further includes the steps of adjusting the ejection rate of the dominant ventricle in accordance with the clock time and the volume-dependent signals from the dominant ventricle and generating control signals for controlling the operation of a blood pump motor associated with the dominant ventricle. The method includes adjusting the ejection rate of the subordinate ventricle in accordance with the adjusted clock rate and the volume-dependent signals received from the subordinate ventricle and generating control signals for controlling a blood pump motor associated with the subordinate ventricle. In this method, the left and right ventricles alternate in operation in response to the control signals generated by the electronic control system. Copulsatile operaton of the two ventricles can of course be controlled in a similar manner. Furthermore, this method is implemented by a microprocessor controlled electronic control system which operates the TCP so that the stroke volume of the dominant ventricle equals the maximum ventricular volume and Starling's law is obeyed.

As will be recognized by one of ordinary skill in the art, it is possible, and may in some cases be desirable, to adjust the described control system so that the dominant ventricle is allowed to fill only partially during the clock time, and in this scheme, the end diastolic volume of the blood pumping chamber is less than the maximum ventricular volume. In this manner of operation, however, cardiac output still outputs venous return (Starling's law). Reference herein to complete filling and maximum ventricular volume are to be read in light of the above-described embodiment.

BRIEF DESCRIPTION OF THE DRAWINGS

The novel features of the invention are set out with particularity in the appended claims, but the invention will be understood more fully and clearly from the following detailed description of the invention as set forth in the accompanying drawings, in which:

DETAILED DESCRIPTION

The present invention is based at least in part on the discovery of a new approach to the control of a blood pump for use in cardiac prostheses. Although this new control approach can be used with any of the known techniques for actuation of blood pumps, for the sake of convenience, this control system will be described in connection with an hydraulically actuated cardiac prosthesis of the type disclosed in prior related U.S. Pat. Nos. 4,369,530 and 4,376,312. Portions of these prior related applications are incorporated herein to illustrate one specific use of the electronic control system of the present invention. It should be clearly understood that the electronic control system is not limited to use with hydraulically actuated blood pumps but can be used in any known blood pump. Also, it should be noted that the actuation method described herein, and the various mechanical forms suitable for practicing it, can be used with equal facility in total cardiac prostheses and circulatory assist devices. Since the similarity of structure and operation of these two classes of devices are well known in the art, the following description of this invention will relate primarily to the hydraulically actuated TCP.

The TCP System

Figure 1:
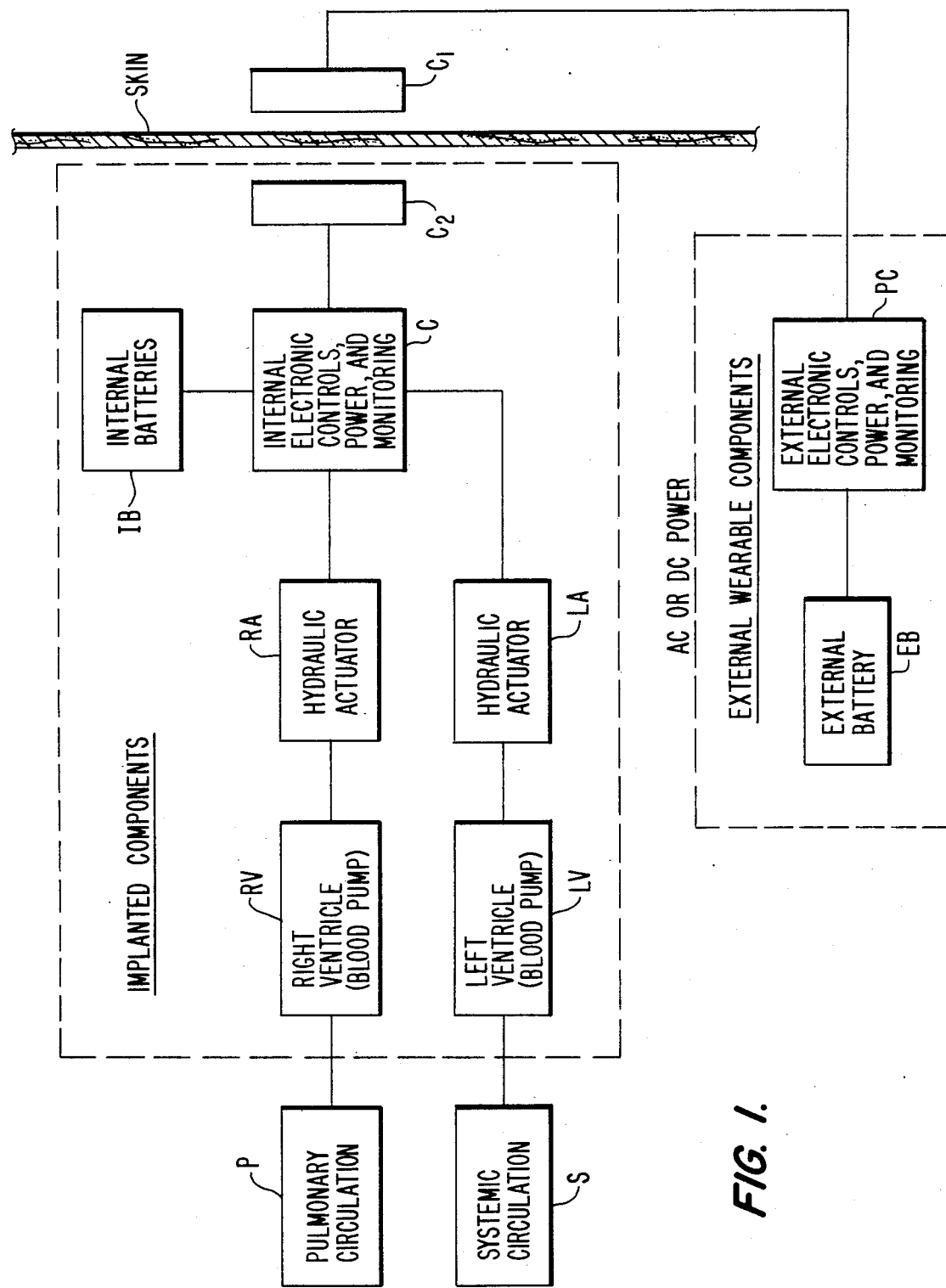
FIG. 1 is a block diagram showing the major components of a total cardiac prosthesis (TCP) system according to the present invention.

FIG. 1 schematically illustrates the basic components of a preferred TCP system according to the invention and the interaction of these components with the physiological systems of the patient. The pulmonary circulation P is maintained by a right ventricular blood pump RV. The systemic circulation S is maintained by a left ventricular blood pump LV. In the preferred embodiment of this invention each of the ventricular blood pumps is powered by a separate hydraulic actuator, RA for the right blood pump and LA for the left blood pump. The operation of the actuators RA and LA is controlled and monitored by an internal electronic control, power and monitoring circuit C which is powered at times by internal batteries IB. Most of the time, however, power is derived from an external power supply comprising an external battery EB and power circuit PC. External battery EB is rechargeable from a conventional power supply, such as household AC current or automotive DC current. Power is delivered transcutaneously to the implanted components by magnetic induction from a primary coil $C_1$ to a secondary coil $C_2$.

Preferably, the blood pumps and actuators are implanted within the thoracic cavity, while the internal electronic controls C and internal batteries IB are implanted outside of the thoracic cavity, preferably near the skin so as to permit easy replacement or servicing of these components by minor surgery. Of course, secondary coil $C_2$ must be located close to the skin for efficient inductive energy transfer.

Blood Pumps

The blood pumps of the preferred TCP system have essentially the same size, configuration and function as the natural heart. These functions include the same stroke volume capability, the same beat rate range, the same atrial filling pressure range and the same arterial pressure range and profile as in a healthy heart.

Blood pumps suitable for use according to this preferred system can be of any of the known designs which are capable of being actuated by hydraulic actuation systems. This class includes systems in which the actuation fluid does work directly on a component of the blood pump as well as those systems in which the hydraulic fluid is coupled to the blood pump by indirect means, such as by magnetic coupling. Of primary interest, however, are those blood pump types in which the hydraulic fluid acts directly on a flexible portion of the blood pump. Examples of this type of blood pump include sac-type and membrane-capped cavity types generally known in the art. The preferred blood pumps for use in the TCP of this invention are of the membrane type (sometimes called bladder-type or sac-type).

These preferred blood pumps essentially comprise a ventricular chamber containing blood inflow and outflow valves. The right and left ventricular blood pumps are generally of the same design except that the housings contain inflow and outflow ducts with orientations necessary to achieve appropriate implantability and fit.

Figure 2:
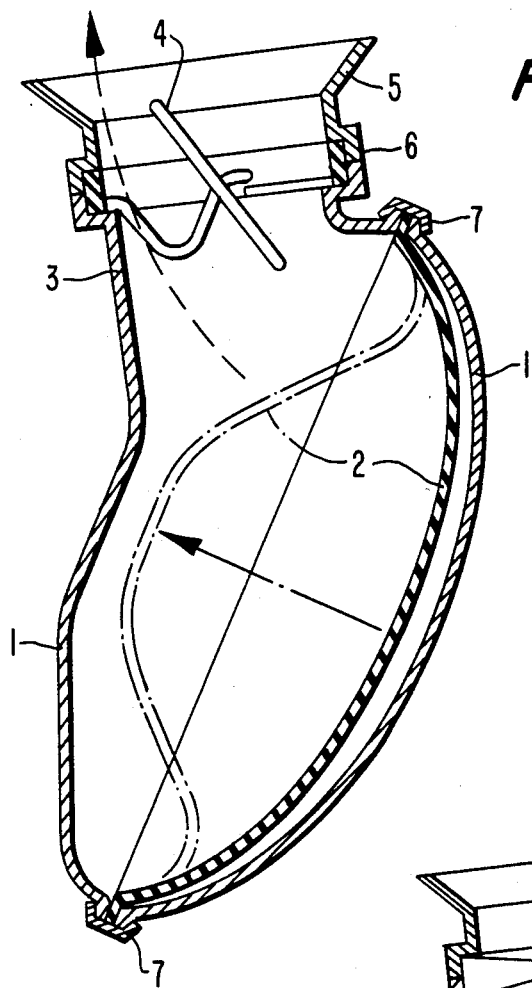
FIG. 2 is a sectional view of one type of blood pump suitable for use in a TCP according to the present invention.

One preferred form of blood pump is schematically illustrated in FIG. 2. The blood pump includes a two-piece rigid housing 1 in which is mounted a flexible membrane, or bladder 2, which is fabricated from an elastomeric material. The housing parts 1 and bladder 2 are secured together at their peripheries by a clamping ring 7. As the blood pump fills with blood during diastole, the flexible membrane assumes the position shown in FIG. 2 in solid lines. As hydraulic fluid is added to the housing on the non-blood side of the membrane (in a manner later described), the change in hydraulic fluid volume causes displacement of the membrane to the position shown in dotted lines. As the membrane is displaced toward the opposite housing wall, blood is forcibly expelled from the blood pump. The membrane should be of such a design that the displacement or deformation occurs uniformly and consistently with each flexing stroke. The membrane also should be designed to intrinsically avoid blood damaging contact with any portion of the rigid housing, and/or extrinsic control means should be provided to so limit the exclusion of the membrane.

The blood pumping chamber is provided with a blood outflow duct 3 containing a suitable prosthetic outflow valve device 4. An inflow duct (not shown) with a suitable prosthetic inflow valve also is provided. An example of suitable mechanical prosthetic valves are Bjork-Shiley valves although numerous other designs also may be employed. The blood pump inflow and outflow tracts preferably are connected respectively to known types of atrial cuffs 5 and arterial grafts (not shown) by snap-on quick-connect fittings 6 of any suitable design which facilitates surgical implantation of the TCP. The cuffs and grafts preferably are anastomosed to the atrial remnant and the aorta or pulmonary artery before the blood pumps are connected thereto.

The blood pumping member 2 preferably is of the single layer type formed from a high strength elastomeric biocompatible material. Polyurethane-based polymers such as Biomer and Avcothane are among the suitable materials for this application. These types of materials have been shown to exhibit high endurance and reliability in blood pumping operations. It is also important that the membrane of the blood pump exhibit low adhesion of thrombus and low generation of thrombo-emboli. The housing is formed of a suitable rigid metallic or plastic material, such as stainless steel coated with polyurethane or other biocompatible coatings, or glass or carbon fiber reinforced plastic. Typically, all internal surfaces of the blood pumps are coated with a suitable biocompatible material.

A suitable blood pump for use in the TCP of the present invention should be capable of providing a range of cardiac outputs of from 2.8 to about 9.5 liters per minute employing full stroke volume and at a beat rate of from about 35 to 120 beats per minute.

Actuation System

In the preferred TCP of the present invention, the above-described blood pumps are hydraulically actuated. While any incompressible fluid which is compatible with the actuator system components can be employed, the preferred actuation fluid is physiologic saline solution (0.9 g percent NaCl) which is very close in saline composition to blood plasma. The use of saline as an actuation fluid eliminates problems associated with the use of certain other actuation fluids such as silicone oils, including diffusion of these oils into the body or diffusion and mixing of body fluids into the actuation fluid which can cause degradation of the polymer materials in the flexible membrane.

The actuation system of the present invention in its most basic form comprises four basic components: (1) an actuation fluid reservoir or compliance sac, (2) actuation fluid pumping means, (3) a ventricular actuation chamber and (4) a flow responsive ventricular dump valve. The basic manner of operation of this system involves the ventricular actuation chamber to displace the flexible blood pump membrane and expel blood from the pump. The ventricular dump valve, which operates in response to actuation fluid flow into the actuation chamber, serves both to close off the actuation chamber outlet during each fluid pulse and to drain or dump the actuation chamber fluid inventory at the end of each pulse, which permits refilling of the blood pumping chamber.

Figure 3:
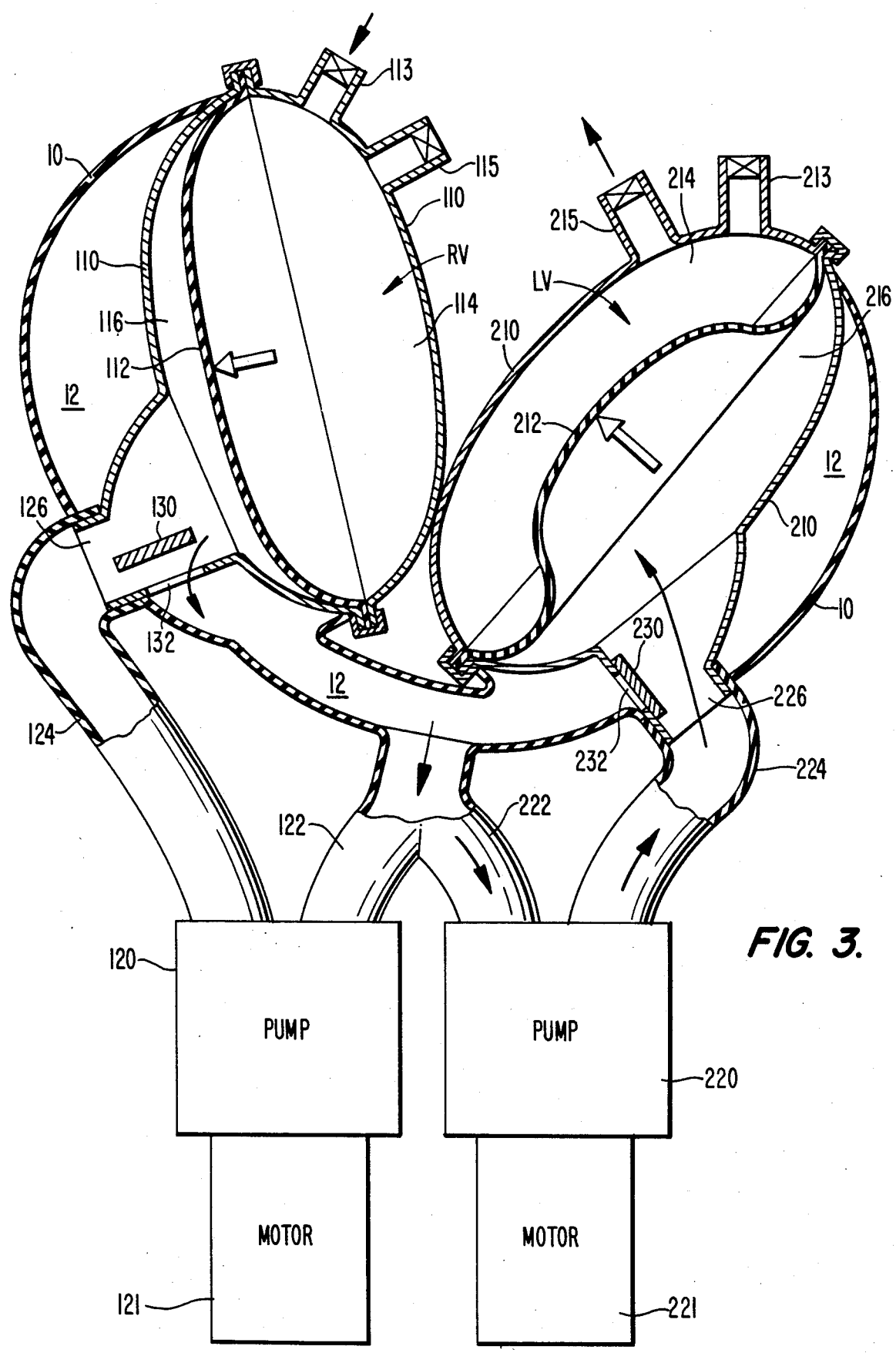
FIG. 3 is a schematic illustration of one embodiment of a total cardiac prosthesis actuation scheme according to the invention.

FIG. 3 schematically illustrates a preferred actuation system for the TCP of the invention. The blood pump includes a right ventricle RV and a left ventricle LV. The right ventricle RV is defined by a rigid housing 110 which is divided by a flexible bladder 112 into a blood pumping chamber 114 and a fluid actuation chamber 116. Similarly, left ventricle LV is defined by a rigid housing 210 which is divided by a flexible bladder 212 into a blood pumping chamber 214 and a fluid actuation chamber 216. Valved blood inlets 113, 213 and valved blood outlets 115, 215 interconnect the blood pumping chambers 114, 214 with the appropriate blood vessels.

Portions of the blood pump housings 110 and 210 are surrounded by a flexible membrane 10 which defines a fluid containing reservoir or compliance sac 12. This compliance sac faces the lung and other soft tissues in the thoracic cavity and contains actuation fluid maintained at normal intrathoracic pressure levels. During operation, the fluid is pumped from each ventricle into the compliance sac during diastole and is removed from the compliance sac during systole. In the preferred form of operation, the ventricles are alternately actuated so as to minimize the change in volume of hydraulic actuation fluid in the system and therefore the overall size of the compliance sac. Copulsatile operation can, of course, be effected if desired.

In the preferred embodiment of FIG. 3, each of the blood pumps is independently actuated by its own driving means which preferably comprises a high speed, mixed flow, rotary pump coupled to a brushless DC motor, although other suitable motor and pump designs may, of course, be used. The pump and motor bearings are totally immersed in and lubricated by the saline actuation fluid. In the preferred embodiment this hydraulic pump is designed to operate at a speed of about 7,000 to 15,000 rpm during the ventricular ejection phase (systole). To effect diastole the pump can be stopped, but it is preferred to provide a pump which can be slowed to about 1,000 to 1,200 rpm. At this low speed the pump will provide insufficient flow to actuate the flow responsive dump valve (described below), yet will maintain a full lubricating fluid film on the bearings.

The operation of the electric motor which drives the hydraulic pumps is continuously controlled in a manner hereinafter described, preferably using back emf commutation of the type described in Chambers et al., "Development of an Electrical Energy Converter for Circulatory Devices," NTIS Publication No. PB-245 042, May, 1975, incorporated herein by reference.

Referring to FIG. 3, actuation pump 120, driven by motor 121, draws fluid from compliance sac 12 through a flexible duct 122 and delivers it to actuation chamber 116 via a flexible duct 124 through inlet 126. Similarly, actuating pump 220 driven by motor 221 draws fluid from compliance sac 12 through a flexible duct 222 and delivers it to actuation chamber 216 via flexible duct 224 through inlet 226. As indicated above, each hydraulic pump is started and operated during systole of its corresponding ventricle and stopped or slowed during diastole of that ventricle.

The actuation chamber is also provided with flow responsive ventricular dump valve means to effect dumping of hydraulic fluid from the actuation chamber at the end of systole. The term "flow responsive" is intended to include those valves which open and close the actuation chamber outlet primarily in response to forces which vary as a function of actuation fluid flow into the actuation chamber. Typically, this flow responsive mechanism will act in response to the pressure or momentum forces created by the incoming actuation fluid or to some combination of these forces. Such a flow actuated valve typically is provided with a threshold bias toward the open position. Accordingly, the valve closes only after the flow associated forces created during initial flow into the actuation chamber exceed this threshold. As long as the forces created by flow of actuation fluid into the actuation chamber are above this threshold, the valve will remain closed—i.e., throughout the systolic phase. When the flow of actuation fluid is stopped or reduced below the threshold bias forces, the bias returns the valve to its open position thereby dumping the actuation fluid from the chamber—i.e., the diastolic phase.

Referring again to the schematic representation in FIG. 3, flow responsive valves 130, 230 are provided adjacent inlets 126, 226, respectively, for controlling the outflow of actuation fluid from actuating chambers 116, 216 into compliance sac 12 through outlets 132, 232. In the operational state shown in FIG. 3, pump 220 is delivering actuator fluid to actuating chamber 216 through inlet 226. This inflow has caused valve 230 to close outlet 232, thereby preventing the escape of actuator fluid from actuating chamber 213. As pump 220 continues to operate, the volume of fluid within actuating chamber 216 increases, thereby compressing blood pumping chamber 214 and forcing blood outwardly therefrom through outlet 215 into the systemic vasculature. At the same time, pump 120 is not actively pumping actuation fluid to actuating chamber 116 through inlet 126. Hence, valve 130 remains in its open position, thereby allowing actuation fluid to drain from actuating chamber 116 into compliance sac 12. The drain of actuating fluid is caused by the right arterial blood pressure, which forces blood into the right ventricular blood pumping chamber 114 through inlet 113. Filling of each blood pumping chamber is therefore passive, as in the natural heart. When pump 120 is activated and pump 220 turned off or slowed down, the left ventricle is permitted to fill, while the right ventricle is compressed to eject blood into the pulmonary system through outlet 115. Of course, the pumps could be operated in copulsatile fashion, as long as a sufficient quantity of actuation fluid is present.

Figure 4:
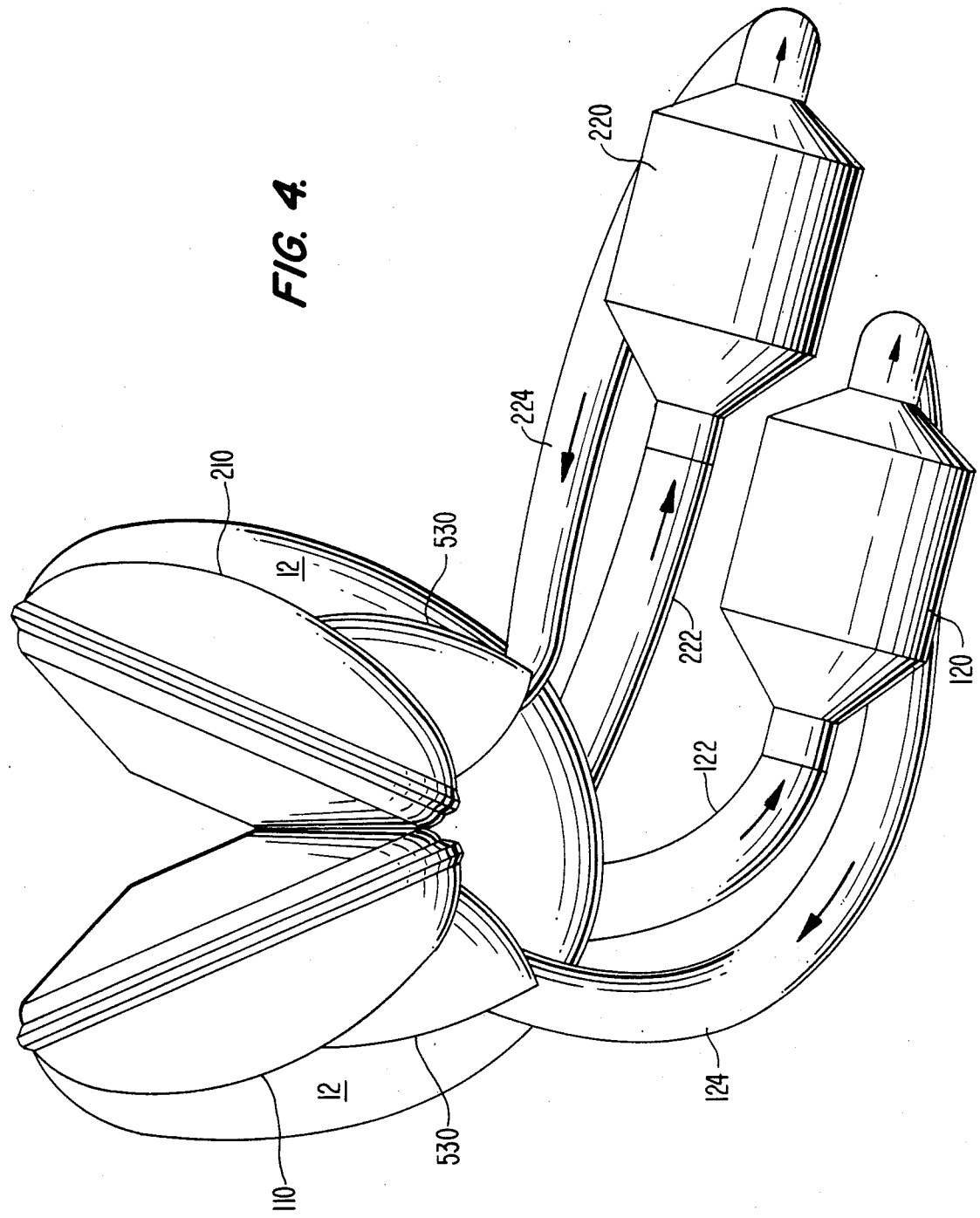
FIG. 4 is a perspective view of one form of the TCP actuation scheme illustrated in FIG. 3.

FIG. 4 illustrates a preferred mechanical configuration for the actuation system embodiment shown schematically in FIG. 3. Flow actuated dump valves 530 are integrally formed on ventricle housings 110, 210. Flexible conduits 122, 124, 222, 224 connect the pumps 120, 220 to dump valves 530 and the compliance sac 12.

Utilization of the above-described preferred embodiment provides a number of significant advantages. Utilization of two independent actuation systems allows for independent ventricular control as well as pump and motor optimization for each ventricle to maximize efficiency. Moreover, the use of flow actuated dump valves provides for the elimination of valve electromechanical actuators and thereby improves the reliability of the resulting TCP.

Figure 5:
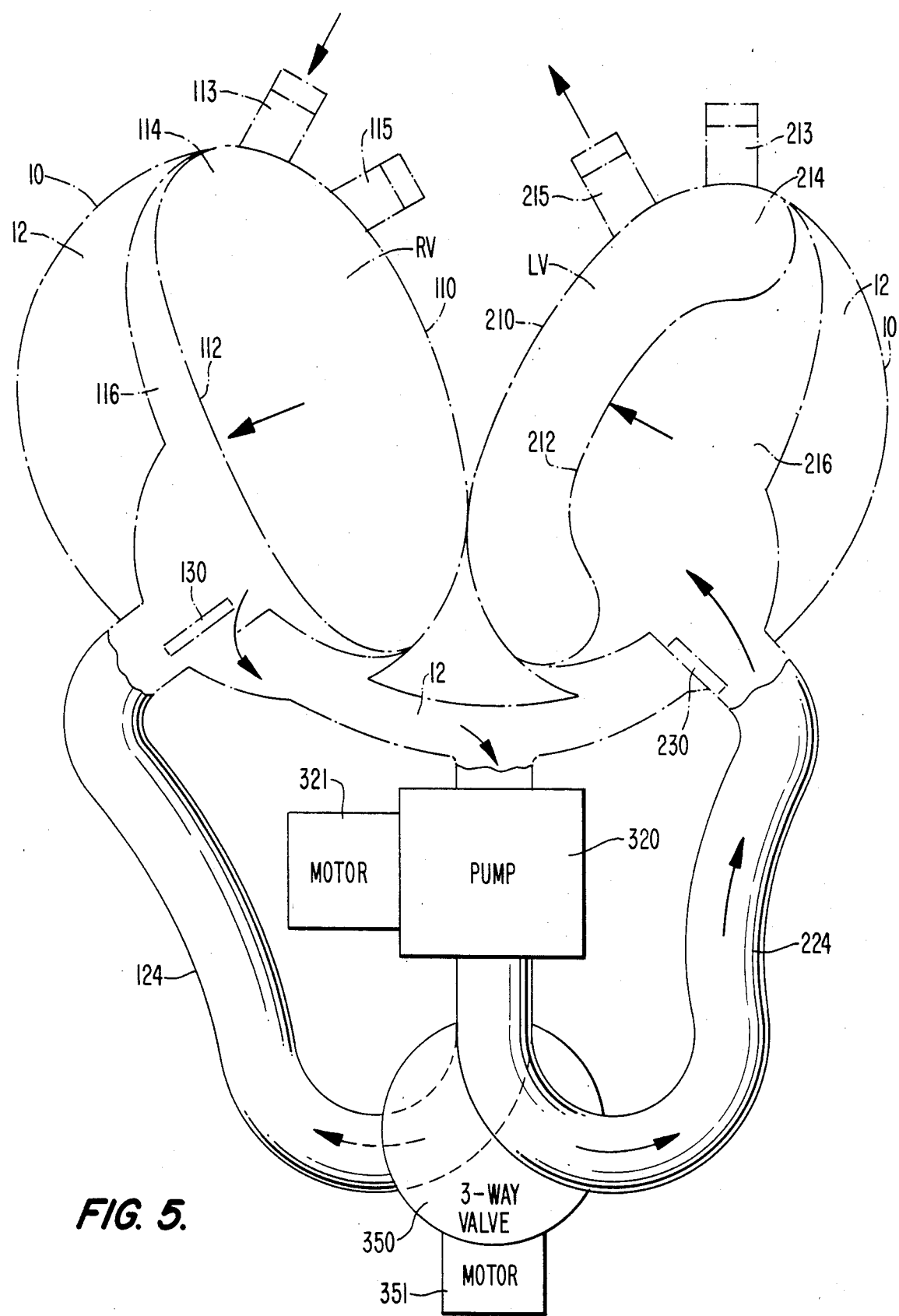
FIG. 5 is a schematic illustration of another embodiment of a total cardiac prosthesis actuation scheme according to the invention.

FIG. 5 schematically illustrates an alternative embodiment in which the portion shown in dot-dash lines is identical to the corresponding portion of the embodiment shown in FIG. 3. In this embodiment a single actuator pump 320 is driven by motor 321. An electromagnetically operated three-way switching valve 350, driven by motor 351, alternatively diverts actuation fluid from the pump outlet to actuating chambers 116, 216 through flexible ducts 124, 224 in response to signals from the control circuit to provide alternate pulses of actuation fluid to the actuation chambers. If copulsatile operation is desired, valve 350 and motor 351 can be eliminated. Flow responsive dump valve 130, 230 used in this system are the same as those described generally above in connection with FIG. 3.

Control and Operation

The above-described TCP system, especially in the preferred embodiments thereof, is particularly advantageous in its ability to respond to electronic controls which are designed to operate the TCP in a manner consistent with natural heart operation in humans. Basically, a modified Frank-Starling mechanism is the sole means of blood pump response to the physiological needs of the implant recipient. Each blood pump ejects whatever blood fills it, and as a result, the atrial pressure and venous return is related to cardiac output in the manner similar to the Frank-Starling response of the normal heart. During normal cardiovascular function, cardiac output is equal to venous return. Since cardiac output is equal to the heart rate times stroke volume, changes in cardiac output can be achieved either by changing the heart rate or the stroke volume. It is preferred according to the present invention to keep the stroke volume constant and achieve changes in cardiac output by changing heart rate.

In the preferred manner of operating the TCP of the present invention, ventricular ejections will alternate thereby minimizing the net volume change per cycle in the compliance sac and minimizing the total volume of necessary actuation fluid. As indicated previously, however, copulsatile operation can be effected with a concomitant increase in the hydraulic reservoir (compliance sac) capacity. One of the significant advantages of the preferred TCP design of the present invention is that by the use of separate actuation mechanisms for each ventricle, separate and optimal control of each ventricle can be achieved.

Figure 6:
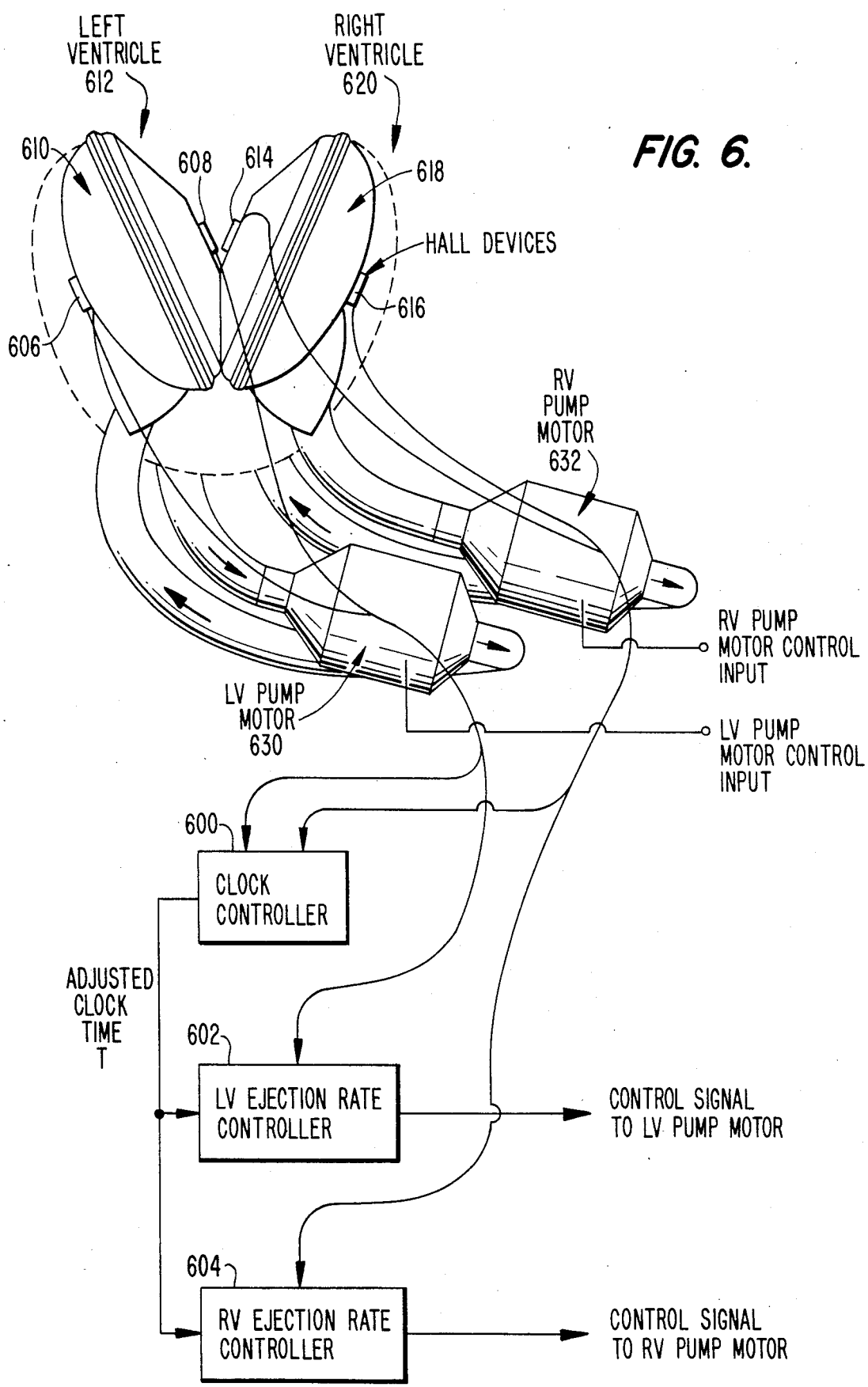
FIG. 6 is a functional block diagram of a TCP control system connected to an hydraulically actuated TCP.

A functional block diagram of the electronic control system for a TCP of the type shown in FIGS. 3-4 is shown in FIG. 6. The electronic control system enables the TCP to respond precisely to the needs of the body by determining the rate of venous return to the heart and making adjustments so that cardiac output is equal to venous return. This objective is accomplished by three controllers, including a clock controller 600, a left ventricle ejection rate controller 602 and a right ventricle ejection rate controller 604.

The clock controller 600 responds directly to changes in filling flow rate, i.e., the intermittent rate of venous return averaged during filling. Venous return is usually averaged over several cycles, and represents the total average rate of blood returning to the heart. Thus, if the diastolic duration is 50 percent of the cycle and no filling takes place during the rest of the cycle, then the average filling flow rate equals twice the venous return. On the other hand, if the diastolic duration is 70 percent, the average filling flow rate is $1/0.7 = 1.4$ times the venous return.

In the preferred embodiment of the electronic control system of FIG. 6, the clock controller 600 is responsive to the filling flow rate of the dominant ventricle, which is normally the left ventricle. In this drawing, for the sake of illustration only, it is assumed that the left ventricle is always the dominant ventricle. Of course, the dominant ventricle can change in response to body requirements, in which case the clock controller 600 would be responsive to the volume of blood in either ventricle, whichever is dominant at that time. As indicated above, the dominant ventricle is the ventricle with the greatest filling flow rate. The left ventricle is expected to be dominant most of the time because the bronchial circulation, which comprises around 5 to 10% of cardiac output, originates off the aorta and shunts back to the left atrium. Thus, the left ventricular output and venous return usually will be greater than that of the right. The clock controller 600 is connected to a pair of Hall effect devices 606 and 608 mounted on opposite sides of the housing 610 of the left or dominant ventricle 612. These Hall effect devices 606 and 608 are also connected to the LV ejection rate controller 602, and another pair of Hall effect devices 614 and 616 are mounted on the housing 618 of the right ventricle 620. These latter Hall effect devices 614 and 616 are connected to the RV ejection rate controller 604.

Figure 7:
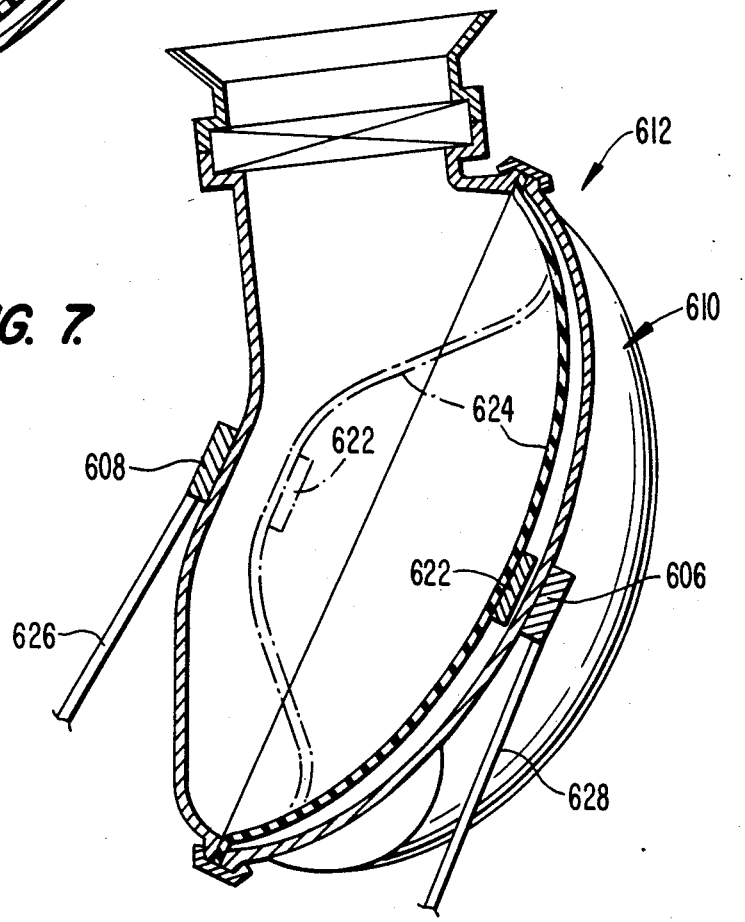
FIG. 7 is a sectional view of a blood pump with Hall effect devices mounted thereon.

The mounting of the Hall effect devices to the left and right ventricle blood pumps is shown in greater detail in FIG. 7. For illustrative purposes, the mounting of these Hall effect devices on the left ventricle blood pump 612 only is shown. Hall effect device 608 is placed on one side of ventricular housing 610. A magnet 622 is placed on the flexible membrane or bladder 624. As the left ventricle blood pump empties, the bladder 624 flexes toward the Hall effect device 608, moving the magnet 622 toward this Hall effect device. The Hall effect device 608 detects the changes in position of the magnet 622 and generates instantaneous position signals which are proportional to the volume of blood as a function of time. These signals are transmitted to the clock controller 600 and the LV ejection rate controller 602 over the electrical lead 626. The other Hall effect device 606 is mounted on the opposite side of housing 610 to detect changes in the position of the magnet 622. As the flexible membrane or bladder 624 flexes toward the compliance sac upon filling, the magnet 622 moves toward the Hall effect device 606, which generates instantaneous position signals proportional to the volume of blood as a function of time and transmits these signals to the clock controller 600 and the LV ejection rate controller 602 over electric lead line 628. In this manner, signals indicating the changes in volume of blood in the left ventricle blood pump 612 as a function of time are generated and supplied to the electronic control system. Although two Hall effect devices are used on each ventricle to generate the volume-dependent signals, one such Hall effect device would be sufficient if sensitive enough to indicate the full range of position changes of the flexible bladder 624. Two such devices are used in the preferred embodiment to provide a detection system with improved sensitivity.

The relationship between the output of the above Hall effect devices 606, 608, 614 and 616 and the displacement of the magnets 622 is a nonlinear function. The gain characteristic of Hall effect devices varies from device to device, so there is no unique mathematical representation for a family of Hall effect devices. Consequently, a process of linear transformation must take place before the information obtained from Hall effect devices can be used to represent the displacement or volume of one of the ventricles. The simplest way to linearize the nonlinear function generated by the Hall effect devices is to calibrate these devices with bench tests to determine the volume and displacement. For example, a look-up table can be generated, which represents the displacement or volume information of a particular Hall effect device. Depending on the particular signal generated by the Hall effect device at any point in time, the displacement or volume information can be determined from the look-up tables.

Although Hall effect devices are preferred in the present invention, other types of sensing devices may be used to generate displacement and volume information. For example, ultrasound devices are known which could be used to generate volume and displacement information for use by the clock controller 600 and the ejection rate controllers 602 and 604.

Returning now to the electronic control system shown in FIG. 6, the clock controller 600 is responsive to the Hall effect devices 606 and 608 (and 614 and 616 when the right ventricle is dominant) to adjust the clock time T or the heart rate of the cardiac prosthesis to allow just enough time for the dominant ventricle, which is assumed to be the left ventricle 612 in FIG. 6, to fill to the desired amount, preferably completely. The clock time T, which is the reciprocal of the heart rate, is the total cycle time for the TCP. The clock controller will decrease the clock time to thereby increase the corresponding heart rate when the average filling flow rate increases. This occurs because only enough time is allowed for the dominant ventricle to fill completely, and no more. If the dominant ventricle fills very quickly, indicating high venous return, then the amount of time in the cycle should be shortened or, in other words, the clock time must be decreased. The subordinate ventricle, which in this case is assumed to be the right ventricle, will not fill as completely because, by definition, it has a slower filling rate, and it is allotted the same interval of time to fill as the dominant ventricle, and thereafter empties completely to a pre-determined volume.

In the preferred mode of operation, the clock controller 600 responds to differences in the actual and desired filling flow rates. This difference forms the controller error signal, which the clock controller 600 constantly attempts to drive to zero, thereby making the actual filling rate equal to the desired rate. Since the electronic control system has no control over venous return, but does have control over the period of time that filling takes place, this filling time is controlled so that the dominant left ventricle fills completely and therefore empties completely to a predetermined volume. The desired filling rate preferably is equal to the maximum ventricular volume (less amounts for leakage and dead volume), which normally will be about 80 ml, divided by the diastolic filling time, which is equal to the diastolic fraction of the cycle times the clock time Tn. The systolic fraction of total cycle length equals f, so the fraction of diastole equals $(1-f)$. In every cycle, the clock controller 600 uses the information generated by the Hall effect devices 606 and 608 to measure the actual average filling rate of the dominant left ventricle during filling, and compares it with the desired filling rate. The error signal is multiplied by the clock controller gain, and this product is added to the old clock time to provide the new, best estimate of the clock time $(T_{n+1})$.

The ejection rate controllers 602 and 604 use the adjusted clock time to adjust the ejection rates of the left and right ventricles. First of all, the clock time can be used to determine the time available for both diastole $((1-f)T)$ and systole $(fT)$. Simply stated, if the blood pumping chamber of the left or right ventricle empties early, it must be slowed down, and when it does not empty completely by the time the allotted systolic interval has elapsed, then it must increase in speed. Although corrections can be made during ejection, for simplicity it is assumed that corrections will be made on the subsequent ejection. In other words, the actual average ejection rate is determined during one ejection cycle from the volume ejected divided by the time it took to eject that volume. Then, at the end of the next filling, the ejection rate controllers 602 and 604 calculate the new desired average ejection rates based on the volume of blood in the ventricles at the end of diastole, divided by the new systolic clock time calculated by the clock controller 600.

In the ejection rate controllers 602 and 604 of the present invention the error signal is defined as the difference between the previous actual ejection rate and the new desired ejection rate. If the new desired ejection rate is less than the previous actual ejection rate, then the blood pumping chamber is slowed down. This can occur if either less blood is in the ventricle at the end of filling, or if the clock time is lengthened. This error signal is multiplied by a gain, which is a function of the ejection rate controllers 602 and 604. The gain is carefully chosen to provide a stable and responsive system which is cognizant of the differences and characteristics of the right and left ventricles and of the differences in the pulmonary and systemic circulations. If the gain is set too high, excessive overshoot and hunting occurs. If the gain is set too low, response times are excessively slow. Thus proper gain adjustment is essential to the establishment of a stable and responsive TCP system.

The ejection rates of the left and right ventricles 612 and 620 of FIG. 6 can be sped up or slowed down by increasing or decreasing the motorspeed of the corresponding pump motor 630 or 632. The LV ejection rate controller 602 is connected to the LV input of the LV pump motor 630, and the RV ejection rate controller 604 is connected to the RV input of the RV pump motor 632. These ejection rate controllers 602 and 604 generate control signals which can change pump motor rpm by changing the applied voltage of a DC motor which is illustrated generally in FIG. 3, or by either pulsed frequency or pulse width modulation. In pulsed frequency modulation, the motor is turned on for fixed intervals of time, but the frequency is changed. In the preferred mode of operation, pulse width modulation is used, where the frequency is a constant, but the duration that the motor is switched on is varied.

Although the clock controller 600, the LV ejection rate controller 602 and the RV ejection rate controller 604 can be hardware implemented or implemented using hydraulic logic, in the preferred embodiment of the present invention, the electronic control system uses a microprocessor to perform the functions of the clock controller 600, the LV ejection rate controller 602 and the RV ejection rate controller 604. A detailed electronics block diagram of the electronic control system of the preferred embodiment is shown in FIG. 8.

Figure 8:
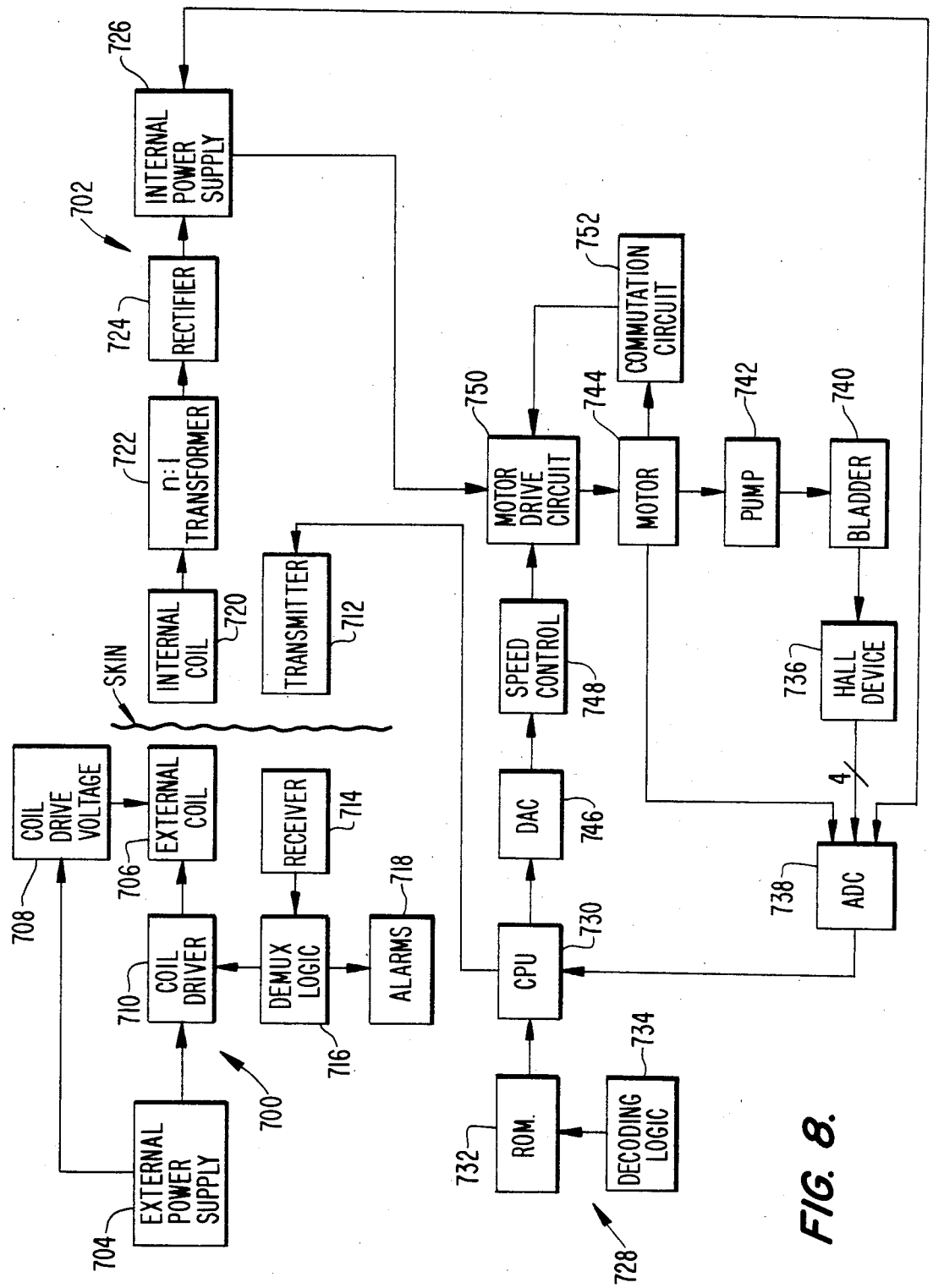
FIG. 8 is a detailed block diagram of the electronic control system.

In the electronic control system of FIG. 8, a tanscutaneous power transfer system is used for transferring power from an external power supply system 700 to an internal power responsive system 702. This transcutaneous power transfer system uses known techniques as described above in connection with FIG. 1. The external power supply system includes a power supply 704, such as external batteries and charging circuits, for driving an external coil 706 at resonance with two, out-of-phase square waves having an amplitude of 24 volts and a frequency of 333 kHz. The power supply 704 supplies one of the square waves to the external coil 706 through a coil drive voltage device 708 and supplies the other square wave through a coil driver 710. The coil driver 710 is responsive to a control signal transmitted transcutaneously from the internal transmitter 712 across the skin to the external receiver 714 to the demultiplexing logic 716. The demultiplexing logic 716 uses conventional modulation techniques to modulate the 333 kHz signal of coil driver 710 with a 1 kHz variable duration square wave derived from the control signal transmitted by the internal transmitter 712 to the external receiver 714. By modulating the signal generated by the coil driver 710, the internal electronic control system, as described in further detail below, controls the transcutaneous power transfer based on internal demand. The internal transmitter 712 also can transmit alarm signals to the receiver 714, which are demodulated by the demultiplexing logic 716, and supplied to alarm circuit 718. These alarm signals can include information on power status, internal battery status, blood pump motor status, physiologic information, etc. The generation of the above control signals and alarm signals by the internal electronic control system will be described in greater detail below.

The external coil 706 is inductively coupled to an internal coil 720, which is juxtaposed therewith under the skin. The external coil 706 functions as a transformer primary winding and the internal coil 720 functions as a transformer secondary winding. The internal coil 720 is connected to a step-down transformer 722 and a full wave rectifier 724. The full wave rectifier 724 supplies power to the internal power supply 726, which includes conventional charge control circuits, an internally charged battery, and voltage drive circuits for supplying the proper voltages to the internal electronics control system. The transcutaneous power transfer system described above is capable of transmitting approximately 35 watts of power from the external power supply system 700 to the internal power responsive system 702 for use by the electronic control system in controlling the actuation of the TCP.

The heart of the electronic control system of FIG. 8 is the microprocessing system 728, which basically includes a central processing unit (CPU) 730, a read-only memory (ROM) 732 and decoding logic 734 for decoding information stored in the ROM 732. The CPU can be any one of a variety of available CPUs, such as the Motorola MC146805, and the ROM can be any available ROM compatible with the particular CPU, such as the Motorola MCM65616. Of course, the CPU 730 includes conventional input and output circuits for receiving and transmitting information, as well as conventional processing circuits for processing the information and performing various data manipulations. Also known decoding logic can be used in conjunction with the CPU 730 and ROM 732 for decoding the information stored in the ROM 732.

The microprocessing system 728 receives signals, which are proportional to the volume of blood in the blood pumping chambers as a function of time, from the Hall effect devices 736, which correspond to the Hall effect devices 606, 608, 614 and 616 of FIGS. 6–7, through analog to digital converter 738. The Hall effect devices 736 are responsive to the changes in position of the bladders or flexible membranes 740 (corresponding to bladder 624 of FIG. 7) of the blood pumping chambers of the left and right ventricles (corrsponding to left and right ventricles 612 and 620 of FIG. 6). The position of these Hall effect devices and their operation in connection with the bladers 740 of the blood pumping chambers were previously described in connection with FIGS. 6 and 7 of the drawings. The microprocessing system also receives data on the condition of the internal power supply 726 through the analog to digital converter 738 and data on the operation of the motors 744, again through the analog to digital converter 738. The pump motors 744 are the DC motors for driving the pumps 742 of the hydraulic actuation system of the TCP, as previously described. For example, a left ventricle pump motor 630 and a right ventricle pump motor 632 were described in connection with the functional block diagram in FIG. 6.

The CPU 730 uses well-known techniques to receive the signals from the Hall effect devices 736 and data from the internal power supply 726 and the motors 744. For example, traditional sample and hold techniques, using a multiple number of channels, can be used. This sample and hold operation can be directly performed by the central processing unit 730 or by the analog to digital converter 738, which can be a single chip data acquisition system currently available on the market.

The microprocessing system 728 supplies control signals to the motors 744 through the digital to analog converter 746, the speed control circuit 748 and the motor drive circuit 750. The CPU 730 uses the signals provided by the Hall effect devices 736 to adjust the clock time T or heart rate of the TCP. The look-up table for the Hall effect devices 736, which was described above in connection with FIG. 7, can be stored in ROM 732 and used by the CPU 730 to determine the volume of blood in the blood pumping chambers. Conventional techniques are employed for using such a look-up table by CPU 730. The CPU 730 changes the clock time or heart rate by first determining the filling flow rate of the dominant ventricle or blood pumping chamber ventricle from the volume of blood in the dominant ventricle as a function of time. The CPU then uses the filling flow rate of the dominant ventricle to adjust the clock time or heart rate to allow the dominant ventricle just enough time to fill completely with blood in response to the venous return. Normally, the dominant ventricle will be the left ventricle, although the dominant ventricle can change during operation of the TCP due to body activities. Thus, the electronic control system, and in particular the CPU 730, must first determine which ventricle is the dominant ventricle from the signals provided by the Hall effect devices 736 and then must adjust the clock time T in accordance with the dominant ventricle.

The CPU 730 next uses the clock time T, and the signals from the Hall effect devices 736, to adjust the left and right ventricle ejection rates so that the left and right ventricles can be completely emptied within the portion of the clock time T allotted to each ventricle. For example, if the systolic fraction f equals 0.4, then the diastolic fraction equals 0.6 and the ventricles must be emptied in (0.4)(T), i.e., the ejection rates must be adjusted to accomplish ejection within the time period (0.4)(T). In this operation, which was described above in connection with FIG. 6, the CPU 730 generates control signals which are supplied to the digital to analog converter 746 and the speed control circuit 748 for controlling the motor drive circuit 750. In the preferred embodiment, the CPU 730 generates pulse width modulation signals for driving the motor drive circuit 750 to provide the appropriate drive voltage to motors 744. Alternatively, the drive circuit 750 can be a power amplifier directly controlled by the CPU 730 through the digital to analog converter 746 or the CPU 730 can produce a DC signal via the digital to analog converter 746 to drive a pulse width modulation circuit which changes motor speed.

A commutation circuit 752 is also provided to generate back EMF signals from the coils of the motor 744 to commutate the motor. A square wave signal is provided by the commutation circuit 752 to the motor drive circuit 750 to start the motor and drive the motor through zero rpm. Back EMF detection of this type has been developed and used in the prior art as described previously in connection with FIG. 3.

The speed control circuit 748 is a modulation circuit which provides pulse width modulation of the back EMF derived control signal supplied to the motor drive circuit 750. The analog signal from the digital to analog converter 746 is supplied to a voltage to frequency converter, which essentially forms the speed control circuit 748. This technique of pulse position modulation of the back EMF derived control signal is known in the art, and allows for direct interface of the CPU 730 with the motor drive circuit 750. The motor drive circuit 750 consists of a number of drive elements, such as VMOS power field effect transistors. Again, drive circuits of this type are generally known in the art.

The motor 744 is a DC brushless motor designed to operate at 10,000 rpm with a maximum operating speed of approximately 15,000 rpm. The windings are actuated by means of the above-described solid state switching system using back EMF commutation, including commutation circuit 752, motor drive circuit 750 and speed control circuit 748. The pump 742 is a mixed flow, centrifugal in-line pump, which pumps fluid from the compliance sac of the TCP via a flexible line through the pump back to the actuation chamber of the blood pumping chamber to effect ventricular ejection. The pump 742 is slowed to approximately 1,200 rpm to allow for ventricular filling during the filling cycle of the blood pumping chamber. The details of the actuation system, which for purposes of illustration is an hydraulically actuated system for actuating a blood pumping chamber having a flexible membrane or bladder, are shown in FIGS. 2-5. As stated previously, other known systems may be used in combination with the electronic control system of the present invention.

The CPU 730 also receives information through the analog to digital converter 738 from the internal power supply 726 and the motors 744. The CPU 730 monitors the power status and battery status of the internal power supply 726 and the motor status of motor 744. This information is used by the CPU 730 to provide output signals through transmitter 712 to the external receiver 714. These signals are then used to set off alarms in the alarm circuit 718, or to control the power supplied from the external power supply system 700 to the internal power responsive system 702. Various techniques known in the art may be used to transmit this information from the transmitter 712 to the receiver 714. Also, it is contemplated that the above telemetry system can be a two-way telemetry system in which information can be transmitted from the external system to the CPU 730 for use in operation of the TCP.

The operation of the electronic control system of FIG. 8 will now be described with reference to the schematic diagrams and flow diagrams of FIGS. 9-13. Preliminarily, it should be noted that the electronic control system of the preferred embodiment controls two alternating ventricles, although similar techniques can be used to control a single ventricle. Also, although the control system of the preferred embodiment alternates ventricular ejections in order to conserve actuating fluid, the diastole period can be made greater than the systole period so that diastoles can overlap but systoles cannot. Furthermore, in the preferred embodiment, the systolic fraction of the total cycle length or clock time T is set at a constant f, but it should be recognized that the control system could be modified to vary the systolic fraction in accordance with body requirements. Finally, as indicated previously, the electronic control system could be used to control copulsatile operation of the ventricles.

The goal of the electronic control system is to implement a control mechanism that makes cardiac output equal to venous return. Since cardiac output (CO) is equal to heart rate (HR) times stroke volume (SV), changes in CO can be achieved by changing either HR or SV. However, if SV is kept to a desired maximum, then changes in CO will be achieved by changes in HR. Since both ventricles of the TCP have the same heart rate, in order for the ventricles to have unequal outputs, one ventricle (the dominant one) must have a greater SV than the subordinate ventricle. Thus, the electronic control system measures ventricular volume as a function of time to control the ventricular ejection rate, selects one of the ventricles as the dominant ventricle, controls the heart rate so the dominant ventricle maintains a maximum stroke volume. Finally, the electronic control system centers the ejection of one ventricle within the middle of the filling duration of the other ventricle to minimize the hydraulic volume excursions within the compliance chamber of the hydraulic actuation system.

The design functions of the electronic control system can best be understood by an analysis of the following mathematical relationships. The analysis begins with the basic premise of the TCP of the present invention that cardiac output is equal to venous return:

$$CO = VR \tag{1}$$

Ejection takes place during the systolic fraction (f) of the cycle, and filling takes place during the diastolic fraction (1−f). Therefore, the actual average ejection rate during ejection (AER) equals:

$$AER = CO/f \tag{2}$$

and the actual average filling rate during filling (AFR) equals:

$$AFR = VR/(1-f) \tag{3}$$

Thus, $$(AER)(f) = (AFR)(1-f) \tag{4}$$

$$AER = (AFR)(1-f)/f \tag{5}$$

The electronic control system is designed to make the dominant ventricle fill completely and empty completely using the maximum ventricular volume (VV). Thus, the clock time T is controlled so that the desired filling rate (DFR) equals:

$$DFR = VV/(1-f)T \tag{6}$$

Each ejection rate controller (see FIG. 6) then controls its respective ventricle to eject the end diastolic volume (EDV) in the desired amount of time (fT):

$$DER = EDV/fT \tag{7}$$

Also, since the electronic control system attempts to make DER=AER and DFR=AFR, equation 4 can be written:

$$(DER)(f) = (DFR)(1-f) \quad (8)$$

and substituting equations 6 and 7 into equation 8:

$$(EDV/fT)(f) = [VV/(1-f)T](1-f) \quad (9)$$

which reduces to:

$$EDV = VV \quad (10)$$

Thus, the resultant end diastolic volume of the dominant ventricle equals the maximum ventricular volume.

The objective of achieving cardiac output equal to venous return is accomplished by adjusting ejection rates so the time average blood flow out of each ventricle is equal to the average blood flow filling the ventricle. Thus, the CPU 730 uses the signals from the Hall effect devices 736 on the dominant ventricle to determine the filling flow rates and then adjusts the clock time T so the dominant ventricle is allowed just enough time to fill completely. The CPU 730 also use the information from Hall effect device 736 to adjust the ejection rate for each ventricle, so each ventricle completely empties within the systolic portion of the clock time T.

Figure 9:
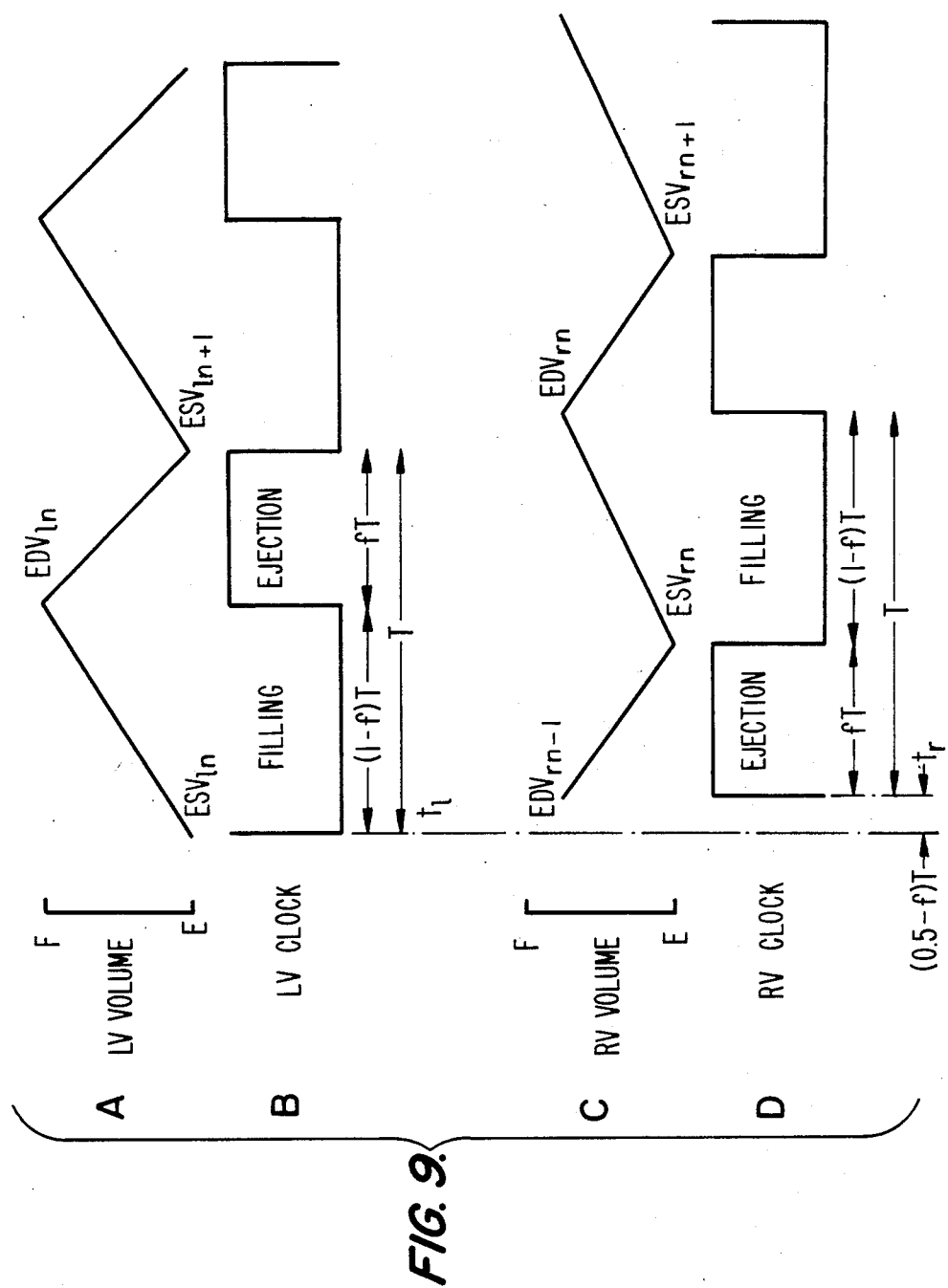
FIG. 9 is a schematic diagram showing ideal volume and clock signals for the left and right ventricles.

In the preferred embodiment, the control system provides for overlapping diastoles. In particular, with a 40 percent systolic duration (f=0.4), the control system provides the idealized volume signals shown in FIG. 9. In FIG. 9, it is assumed that the left ventricle is the dominant ventricle because it fills faster. The clock time T in seconds and heart rate (1/T) are adjusted so the dominant ventricle can fill in (1−f)T seconds, where f is the preset systolic fraction of the cycle length. Lines A and B of FIG. 9 show the left ventricle volume and clock, respectively. After the left ventricle fills in the time period (1−f)/T, the CPU 730 uses the signals obtained from the Hall effect devices 736 and the adjusted clock time T to adjust the ejection rate of the left ventricle to empty the left ventricle in fT seconds.

Similarly, the subordinate or right ventricle is allowed the same amount of time to fill as the dominant ventricle, i.e., (1−f)F, but it will not fill completely. The right ventricle volume and clock relationship are shown in lines C and D of FIG. 9. The CPU 730 uses the signals obtained from the Hall effect devices 736 on the right ventricle and the adjusted clock time T to adjust the ejection rate of the right ventricle, so the amount of blood in the ventricle at the end of filling will be ejected in fT seconds. Thus, each ventricle obtains its own separate timing signals from the clock, which determines the beginning of filling and of ejection. In addition, if a pump empty condition occurs before the clock time runs out, an empty signal is generated in response to the signals provided by the Hall effect devices 736.

Figure 10:
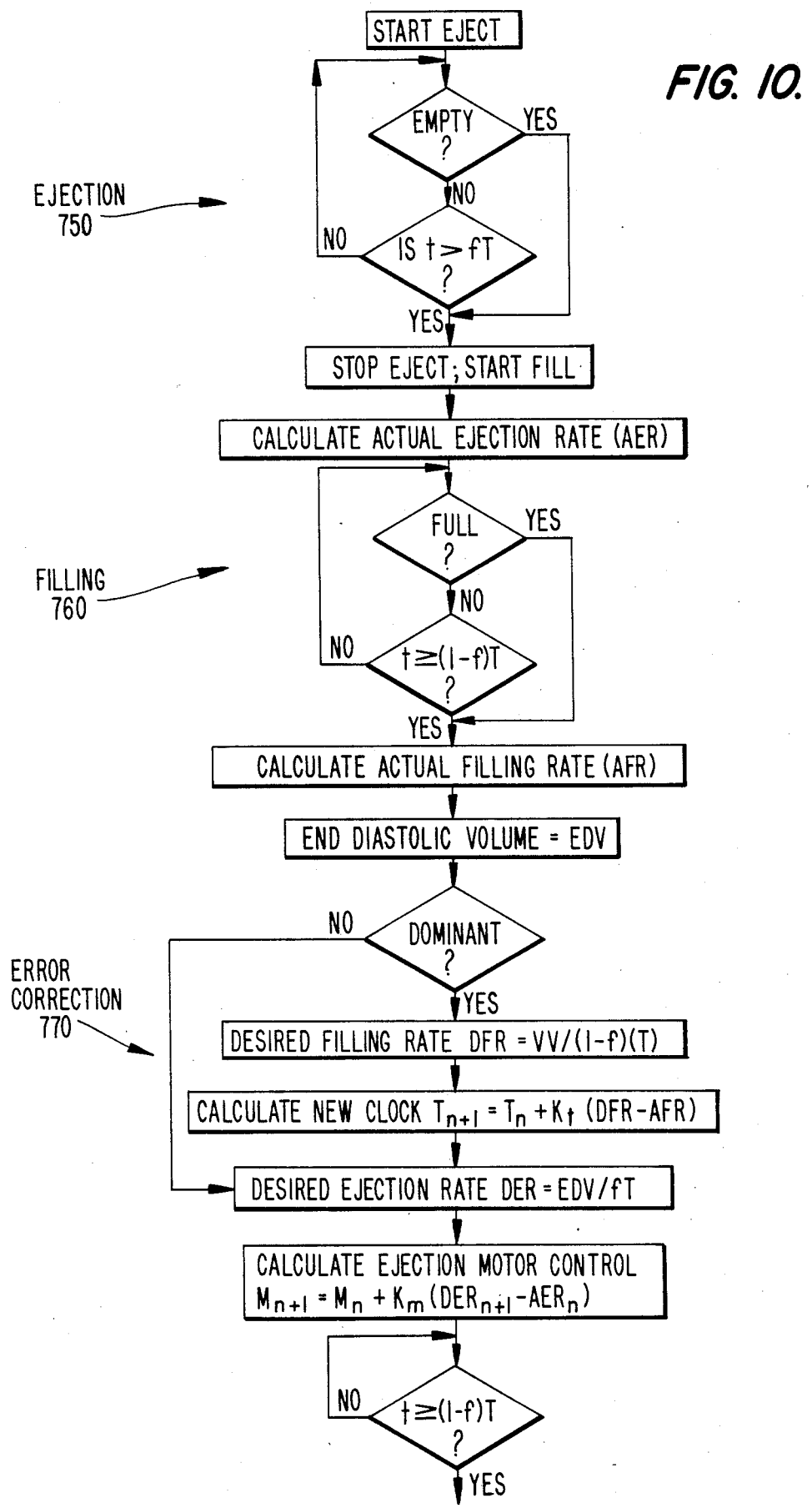
FIG. 10 is a flow diagram for the TCP control system for controlling a single ventricle.

The basic flow diagram for the control system of FIG. 8, assuming operation for a single ventricle, is shown in FIG. 10. The additional logic required for operation of two ventricles, as well as additional details, is shown in the flow diagram of FIG. 11. Referring first to the flow diagram in FIG. 10, the operation of the ventricle under the control of the CPU 730 can be divided into the ejection, filling and error correction modes.

During the ejection mode 750, the volume-dependent signals provided by the Hall effect devices 736 are checked to determine if the pump is empty. If the pump is empty, ejection is terminated and, if it is not, the time T is checked to determine if the amount of time for ejection (fT) has run out. If the time has run out, ejection is terminated and filling starts immediately. The actual average ejection rate (AER) is then calculated from the end diastolic volume (EDV) before ejection, minus the end systolic volume (ESV) after ejection, divided by the actual time of ejection.

This latter step begins the filling mode 760 in FIG. 10. The signals provided by the Hall effect devices 736 are checked to determine if the pump is full or if the allowed filling time (1−f)T has run out, then the actual filling rate (AFR) is calculated from the EDV after filling, minus ESV before filling, divided by the actual filling time.

The error correction mode 770, shown in FIG. 10, can be divided into clock control and ejection rate control. The clock time T is only corrected if the ventricle is the dominant ventricle, which is the ventricle having the largest average filling rate. The new clock time is calculated from the old clock time, plus a clock controller gain ($K_t$), times an error signal. The error signal is the desired minus the actual filling rates (DFR−AFR), where the desired filling rate is equal to the maximum ventricular volume (VV), divided by the desired filling time (1−f)T. Once the clock time T is determined, the desired ejection rate (DER) can be calculated from the end diastolic volume (EDV), divided by the desired ejection time (fT). Next, as shown by the next to last step in FIG. 10, the actuator motor control signal ($M_{n+1}$) is determined from the previous signal, plus a motor controller gain ($K_m$), times an error signal. The error consists of the difference between the next desired ejection rate (DER) and the previous actual ejection rate (AER).

After the errors are calculated, the final step of FIG. 10 occurs, which determines whether the diastolic clock interval (1−f)T has elapsed. Ejection from the ventricle cannot begin until this time interval has elapsed. Alternatively, if the clock time has already elapsed, ejection can begin immediately and then, a few milliseconds later, after the control signals are calculated, a correciton can be made to the ejection rate.

Figure 11A:
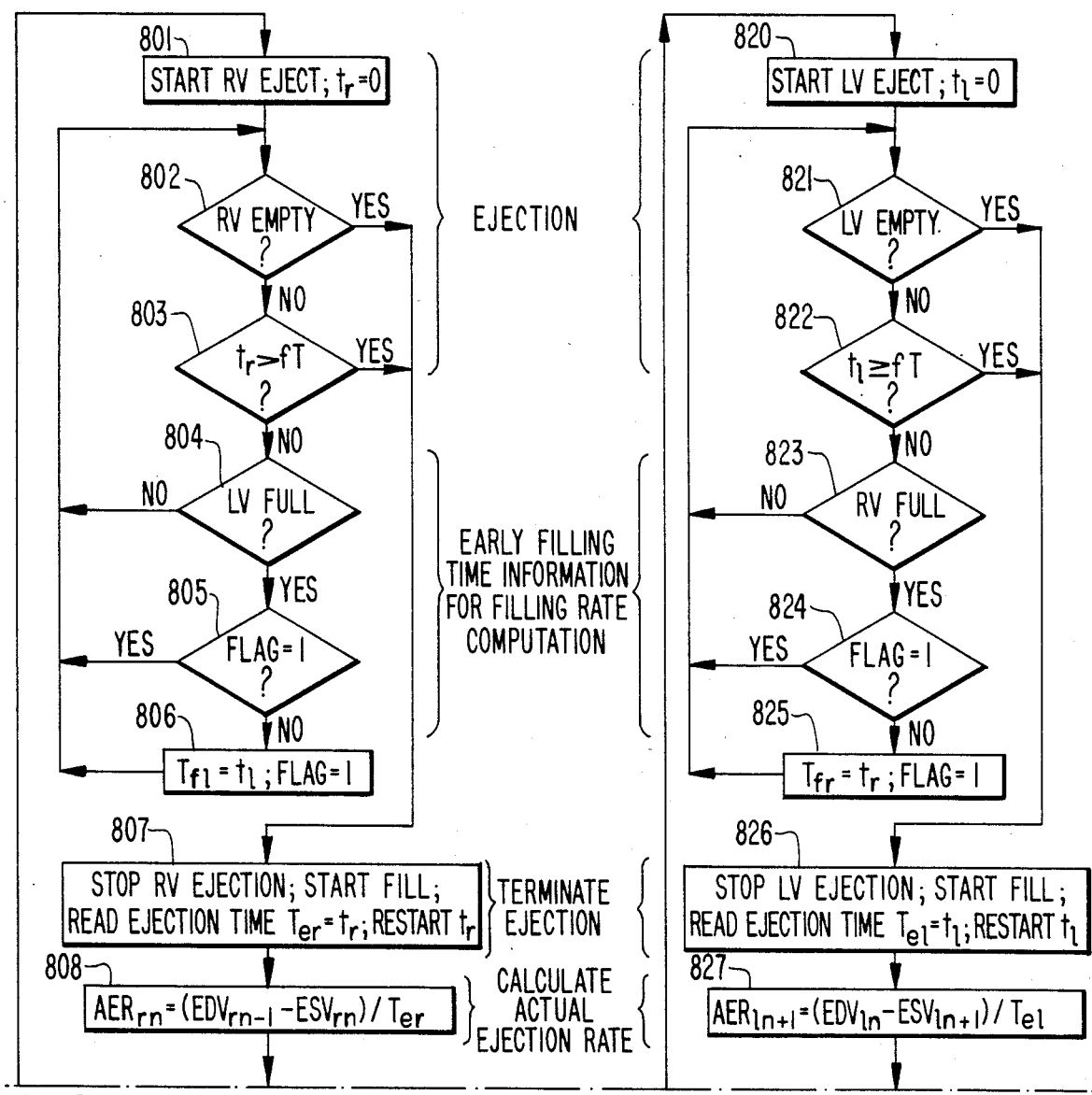
FIG. 11 is a detailed flow diagram for the TCP control system for controlling both the left (dominant) and right (subordinate) ventricles.
Figure 11B:
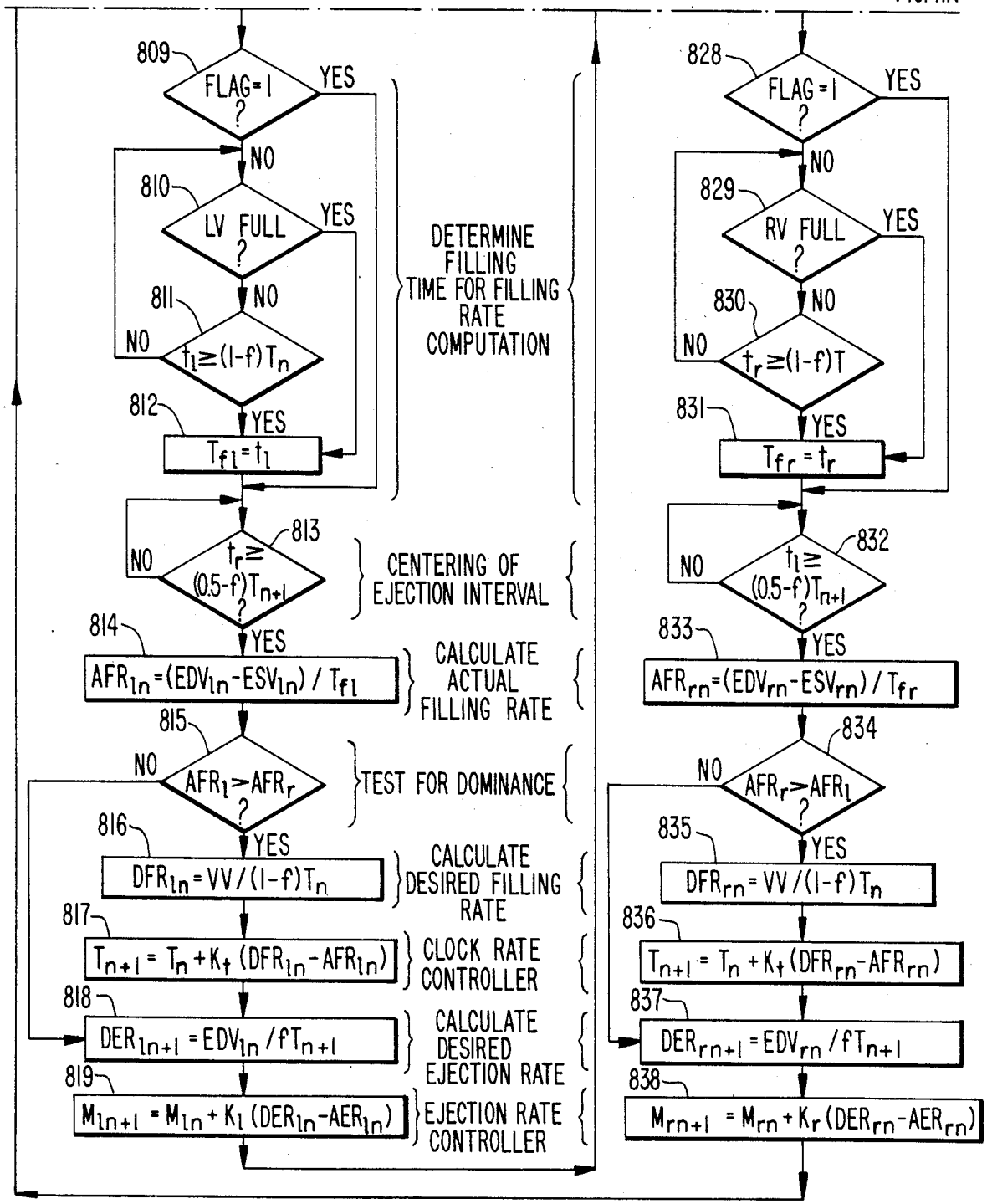

The detailed flow diagram for filling one ventricle simultaneously with the ejection of the opposite ventricle is shown in FIG. 11. The filling of the left ventricle, which starts in step 826 and continues through step 804 to step 811, occurs simultaneously with the ejection of the right ventricle, which begins in step 801 and ends in step 807. Similarly, the filling of the right ventricle starts at step 807 and goes through step 830. This overlaps with the ejection of the left ventricle, which begins in step 820 and continues through step 826.

The flow diagram in FIG. 11 begins with the ejection of the right ventricle in step 801, which occurs during the filling of the left ventricle. If the right ventricle is empty at step 802, or the systolic duration (fT) has expired at step 803, ejection is terminated. Meanwhile, if the left ventricle fills before the right ventricle is empty, the early filling flag is set (FLAG), and the actual filling time ($T_{fl}$) is determined in steps 804–806. The early filling flag is used so that the actual filling time $T_{fl}$ will be determined only once. After ejection in step 807, the actual ejection rate of the right ventricle is determined in step 808 from the ratio of the end diastolic volume before ejection, minus the end systolic volume after ejection ($EDV_{rn-1} - ESV_{rn}$), divided by the actual ejection time ($T_{er}$).

The early filling flag is checked again in step 809 and, if it is set, meaning that the left ventricle is already full, then the actual filling rate is calculated in step 814. If the left ventricle is not full, then the flag will not equal one, and the left ventricle will continue to be checked to determine if it is full at step 810 or if the diastolic duration $(1-f)T_n$ has run out at step 811. The actual filling rate ($AFR_{ln}$) of the left ventricle then is determined from the volume of blood during filling, which is equal to the end diasolic volume after filling, minus the end systolic volume before filling, divided by the actual filling time at step 814.

At step 815, the left ventricle is tested to determine if it is dominant, i.e., whether the average filling rate ($AFR_l$) of the left ventricle is greater than the average filling rate ($AFR_r$) of the right ventricle. The clock duration or cycle length $T_n$ will only be changed if the left ventricle is dominant. The objective is to control the cycle length or clock time $T_n$ so that the desired filling rate at step 816 is equal to the maximum ventricular volume VV, divided by the diastolic duration $(1-f)T_n$. This assures that the dominant ventricle has just enough time to fill completely. The new clock time $(T_{n+1})$ is then determined from the previous time $(T_n)$, plus the clock controller gain ($k_t$), times an error signal, as indicated in step 817. The error signal is the difference between the desired filling rate from step 816 and the actual filling rate from step 814. Once the cycle length $T_n$ is known, then the new desired ejection rate ($DER_{ln+1}$) can be determined in step 818 from the end diastolic volume, or the amount of blood to be ejected, divided by the new amount of time allowed for ejection ($fT_{n+1}$). Then the new motor control voltage ($M_{ln+1}$) for the ejection of the left ventricle is determined from the previous motor control voltage, plus an error signal, times the motor controller gain, as set forth in step 819. The error signal consists of the difference between the up-coming desired ejection rate ($DER_{ln+1}$), minus the last actual ejection rate ($AER_{ln}$). Step 813 is used to center the ejection interval of one ventricle in the middle of the diastolic interval of the other. Thus, ejection of the left ventricle is now ready to begin in step 820, while the right ventricle continues to fill.

The ejection of the right ventricle and the calculation of the new motor control voltage ($M_{rn+1}$) for the ejection of the right ventricle in steps 820–838 parallels steps 801–819 for the left ventricle. Also, step 832 is provided to center the ejection interval of one ventricle in the middle of the diasolic interval of the other ventricle. This latter step corresponds to step 813.

Figure 12:
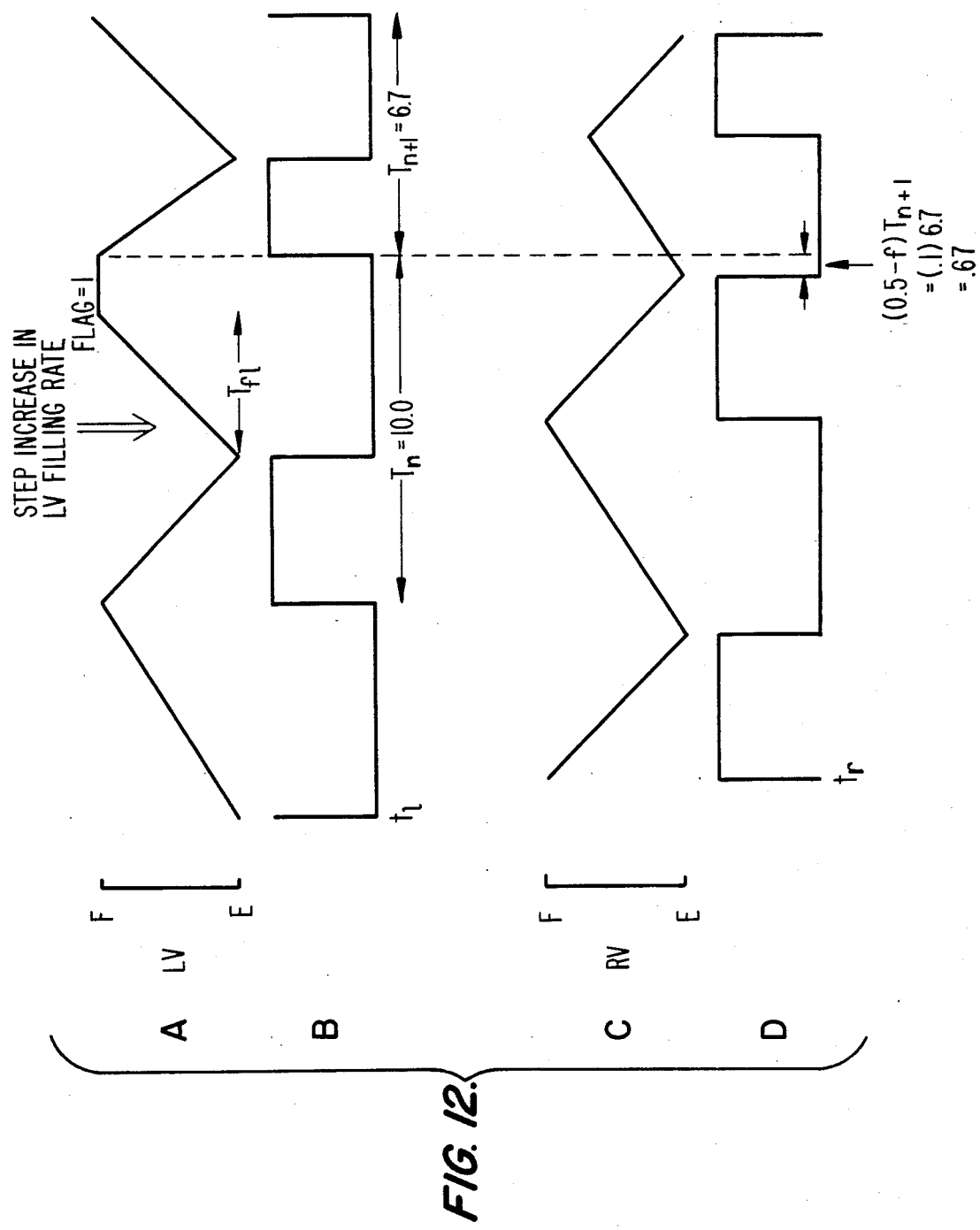
FIG. 12 is a timing diagram illustrating the response of the TCP to an increase in the left (dominant) ventricle filling rate.
Figure 13:
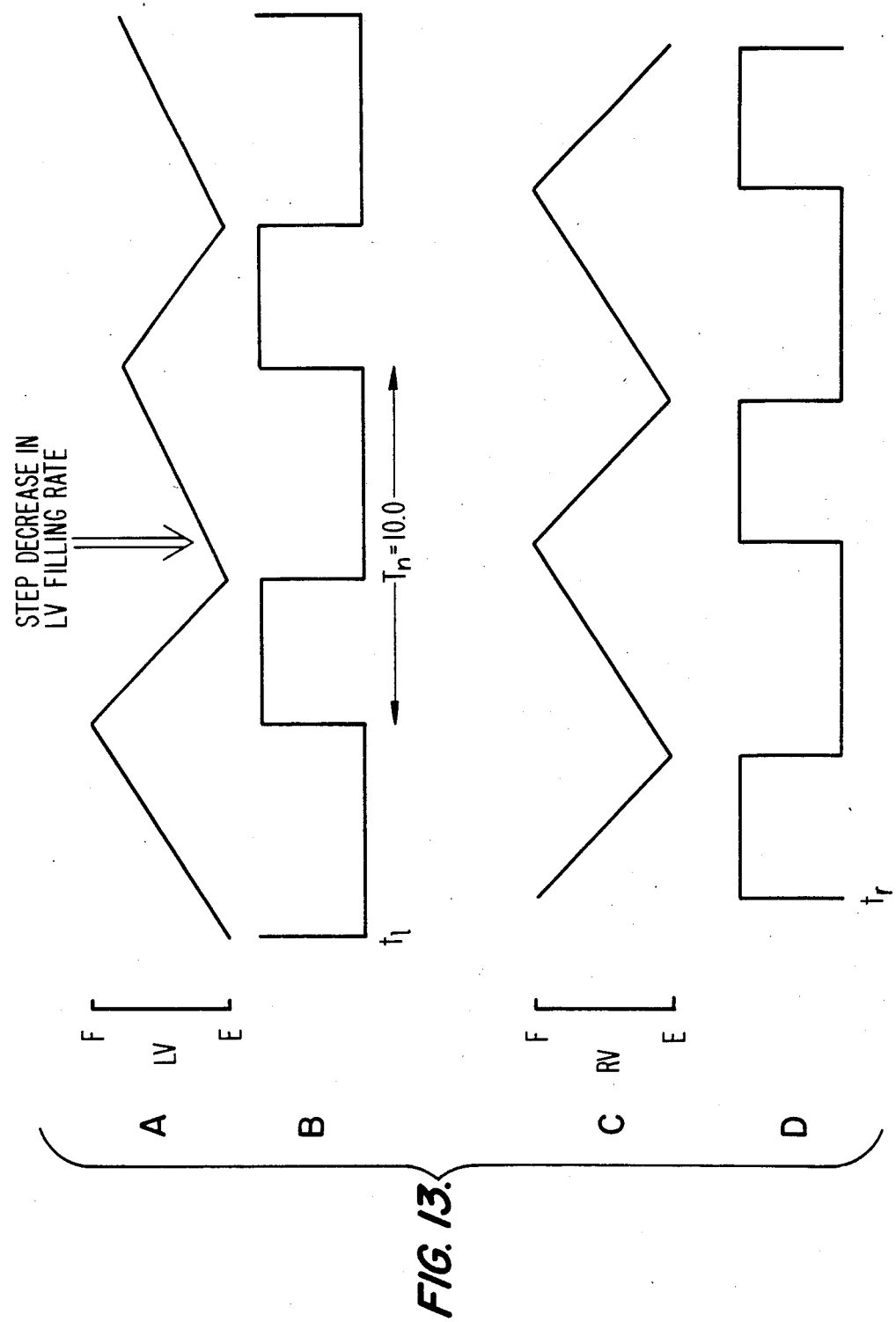
FIG. 13 is a timing diagram illustrating the response of the TCP to a decrease in the left (initially dominant) ventricle filling rate and an increase in the right (eventually becomes dominant) ventricle filling rate.

Idealized wave forms for the responses of the left and right ventricles to a step increase and a step decrease in left ventricle filling rates are shown in FIGS. 12 and 13. As shown in lines A and B of FIG. 12, the left ventricle fills before expiration of the time period of the clock $T_n$. As a result, the control system, through the CPU (730), calculates a new clock time $(T_{n+1})$, which increases the heart rate so that the left ventricle, which is the dominant ventricle, is allowed just enough time to fill completely. Then, as shown in lines C and D, because of this change in the heart rate, the right ventricle will not fill completely.

In lines A and B of FIG. 13, a step decrease in the left ventricle filling rate is shown. In accordance with step 811 of FIG. 11, the CPU 730 of the TCP controller waits for the expiration of the time period before moving on to calculate the actual filling rate. The right ventricle, as shown in lines C and D of FIG. 13, continues to operate normally, and the only change is that the left ventricle no longer fills completely.

In summary, the electronic control system shown in FIG. 8 is responsive to venous return to the TCP to control the TCP to provide cardiac output equal to the venous return. This control occurs by adjusting the heart rate of the TCP in accordance with the filling flow rate of the dominant ventricle so that the dominant ventricle is allowed just enough time to fill completely. In other words, the end diastolic volume of the dominant ventricle is controlled so that it equals the maximum ventricular volume. The ejection rates of the left and right ventricles then are adjusted to eject all blood in the systolic time period determined by the adjusted clock time by generating appropriate control signals for the pump motors. These pump motors then drive actuation system for the blood pumping chambers.

While certain specific embodiments of the invention have been described with particularity herein, it should be recognized that various modifications thereof will appear to those skilled in the art. Therefore, the scope of the invention is to be limited solely by the scope of the claims appended hereto.

We claim:

1. In combination with an implantable hydraulic actuation system for supplying motive power to at least one blood pumping chamber, said hydraulic actuation system including an actuation fluid reservoir, an actuation chamber in fluid communication with said actuation fluid reservoir and an actuation fluid pump in fluid communication with said actuation fluid reservoir and said actuation chamber for pumping fluid from said actuation fluid reservoir to said actuation chamber to eject blood from said blood pumping chamber, an electronic control system comprising:

means for receiving power;

sensing means associated with said blood pumping chamber for determining the volume of blood in said blood pumping chamber as a function of time during both filling and emptying of said blood pumping chamber and generating volume related signals;

clock controller means coupled to said sensing means for determining the filling flow rate of said blood pumping chamber as a function of the volume related signals from said sensing means and adjusting the heart rate at which said blood pumping chamber fills and empties to allow just enough time for said blood pumping chamber to fill to a predetermined capacity;

ejection rate controller means coupled to said sensing means and said clock controller means for adjusting the ejection rate of said blood pumping chamber as a function of the adjusted heart rate of said blood pumping chamber and the volume related signals and generating control signals to control the ejection of blood from said blood pumping chamber in accordance with the adjusted ejection rate of said blood pumping chamber; and pump motor means coupled to said ejection rate controller means for driving said actuation fluid pump, said pump motor means being responsive to the control signals from said ejection rate controller means to enable said actuation fluid pump to eject blood from said blood pumping chamber in accordance with the adjusted ejection rate.

2. In combination with an implantable hydraulic actuation system for supplying motive power to at least one blood pumping chamber, said hydraulic actuation system including an actuation fluid reservoir, an actuation chamber in fluid communication with said actuation fluid reservoir and an actuation fluid pump in fluid communication with said actuation fluid reservoir and said actuation chamber for pumping fluid from said actuation fluid reservoir to said actuation chamber to eject blood from said blood pumping chamber, an electronic control system comprising:

means for receiving power;
  sensing means associated with said blood pumping chamber for determining the volume of blood in said blood pumping chamber as a function of time during both filling and emptying of said blood pumping chamber and generating volume related signals;
  programmed microprocessor control means coupled to said sensing means for generating control signals in response to the volume related signals from said sensing means, said programmed microprocessor means including clock control means for determining the filling flow rate of said blood pumping chamber in response to the volume related signals and adjusting the heart rate at which said blood pumping chamber fills and empties to allow just enough time for said blood pumping chamber to fill to a predetermined capacity and ejection rate control means responsive to the adjusted heart rate and the volume related signals for generating control signals which adjust the blood ejection rate of said blood pumping chamber so that the blood in said blood pumping chamber can be ejected in accordance with the adjusted heart rate; and
  pump motor means coupled to said programmed microprocessor control system for driving said actuation fluid pump, said pump motor means being responsive to the control signals from said programmed microprocessor control means to enable said actuation fluid pump to eject blood from said blood pumping chamber in accordance with the adjusted ejection rate.

3. In combination with an implantable hydraulic actuation system for supplying motive power to at least one blood pumping chamber, said hydraulic actuation system including an actuation fluid reservoir, an actuation chamber in fluid communication with said actuation fluid reservoir and an actuation fluid pump in fluid communication with said actuation fluid reservoir and said actuation chamber for pumping fluid from said actuation fluid reservoir to said actuation chamber to eject blood from said blood pumping chamber, an electronic control system comprising:

means for receiving power;
  sensing means associated with said blood pumping chamber for generating signals related to the volume of blood in said blood pumping chamber as a function of time;
  data processing means coupled to said sensing means for generating control signals in response to the volume-related signals from said sensing means, said data processing means being responsive to the volume-related signals to determine the filling flow rate of said blood pumping chamber and adjust the heart rate at which said blood pumping chamber fills and empties to allow just enough time for said blood pumping chamber to fill to a predetermined volume, said data processing means further generating control signals which adjust the blood ejection rate of said blood pumping chamber so that the blood in said blood pumping chamber can be ejected in accordance with the adjusted heart rate; and
  pump motor means coupled to said data processing means for driving said actuation fluid pump, said pump motor means being responsive to the control signals from said data processing means to enable said actuation fluid pump to eject blood from said blood pumping chamber in accordance with the adjusted ejection rate.

4. The combination of claims 1, 2 or 3 wherein said hydraulic actuation system supplies motive power to a dominant and subordinate blood pumping chamber, the dominant blood pumping chamber being the blood pumping chamber with the highest filling flow rate, said electronic control system further comprising means for controlling the heart rate of said dominant andd subordinate blood pumping chambers in response to the filling flow rate of said dominant blood pumping chamber to allow just enough time for said dominant blood pumping chamber to fill completely, said electronic control system further generating control signals to control the blood ejection rates of said dominant and subordinate blood pumping chambers in accordance with the adjusted heart rate and the volume related signals from said dominant and subordinate blood pumping chambers, said pump motor means driving said actuation fluid pump to eject blood from said dominant and subordinate blood pumping chambers in accordance with the adjusted ejection rates.

5. The combination of claim 4 wherein said electronic control system further comprises means responsive to the volume related signals from sensing means associated with each of said blood pumping chambers to determine which of said blood pumping chambers has the highest filling flow rate, said electronic control system selecting the blood pumping chamber with the highest filling flow rate as said dominant blood pumping chamber.

6. The combination of claim 4 wherein said electronic control system further comprises means for driving said dominant and subordinate blood pumping chambers alternately.

7. The combination of claim 6 wherein said electronic control system further comprises means for driving said first and second blood pumping chambers such that their systolic time period equals their diastolic time period.

8. The combination of claim 6 wherein said electronic control system further comprises means for driving said first and second blood pumping chambers such that the diastolic time periods of said dominant and subordinate blood pumping chambers overlap.

9. The combination of claim 4 wherein said electronic control system further comprises means for repetitively adjusting the ejection rates of said dominant and subordinate blood pumping chambers for use in the ejection of blood during the next systolic time period allotted to each of said dominant and subordinate blood pumping chambers.

10. The combination of claims 1, 2 or 3 wherein said means for receiving power comprises a secondary coil and said electronic control system further comprises power means for applying electrical power to said electronic control system, said power means including a primary coil adapted to be inductively coupled to said secondary coil for transmitting electronic power across the intact skin of a patient.

11. The combination of claims 1, 2 or 3 wherein said blood pumping chamber includes a flexible bladder and said sensing means comprises a magnet mounted on said flexible bladder and at least one Hall effect device mounted on said blood pumping chamber to detect the displacement of said flexible bladder by detecting changes in the position of said magnet, said Hall effect devices generating volume related signals as a function of time in accordance with the instantaneous changes in position of said magnet.

12. In an implantable cardiac prosthesis having at least one blood pumping chamber which fills in response to body requirements and an actuation means for ejecting blood from said pumping chamber, a control system for controlling said actuation means, said control system comprising:

sensing means adapted to be coupled to said blood pumping chamber for determining the volume of blood in said blood pumping chamber as a function of time and generating volume-related signals;

control means coupled to said sensing means for determining the filling flow rate of said blood pumping chamber from the volume-related signals and adjusting the heart rate at which said blood pumping chamber fills and empties to allow just enough time for said blood pumping chamber to fill to a predetermined volume, said control means further generating control signals which adjust the blood ejection rate of said blood pumping chamber in response to the adjusted heart rate; and driving means coupled to said control means for driving said actuation device in response to the control signals from said control means to eject blood from said blood pumping chamber in accordance with the adjusted blood ejection rate.

13. A control system according to claim 12 wherein said control means comprises an electronic logic control.

14. A control system according to claim 13 wherein said electronic logic control comprises programmed microprocessor means for generating control signals.

15. A control system according to claim 14 wherein said at least one blood pumping chamber includes a first blood pumping chamber and a second blood pumping chamber, and wherein said sensing means is further adapted to provide first and second volume-related signals indicative of the volume of blood in said first and second blood pumping chambers, respectively, said programmed microprocessor means further comprising means responsive to said first and second volume-related signals for determining the filling flow rate of said first and second blood pumping chambers, respectively, and selecting the one of said first and second blood pumping chambers with the highest filling flow rate as the dominant blood pumping chamber and the other as the subordinate blood pumping chamber.

16. A control systeml according to claim 15, wherein said programmed microprocessor means further comprises means for controlling the heart rate of said dominant and subordinate blood pumping chambers in response to the filling flow rate of said dominant blood pumping chamber to allow just enough time for said dominant blood pumping chamber to fill completely.

17. The control system of claim 16 wherein said programmed microprocessor means further comprises means for driving said dominant and subordinate blood pumping chambers alternately.

18. The control system of claim 17 wherein said microprocessor means further comprises means for driving said blood pumping chambers such that the systolic time period equals the diastolic time period of said blood pumping chambers.

19. The control system of claim 17 wherein said microprocessor means further comprises means for driving said blood pumping chambers such that the diastolic time periods of said dominant and subordinate blood pumping chambers overlap.

20. The control system of claim 16 wherein said programmed microprocessor means further comprises means for repetitively adjusting the ejection rates of said dominant and subordinate blood pumping chambers for use in the ejection of blood during the next systolic time period allotted to said dominant and subordinate blood pumping chambers.

21. The control system of claim 12 wherein said means for receiving power comprises a secondary coil and wherein said control system further comprises power means for applying electrical power to said electronic control system, said power means including a primary coil adapted to be inductively coupled to said secondary coil for transmitting electrical power across the intact skin of a patient.

22. The control system of claim 14 wherein said blood pumping chamber includes a flexible bladder and said sensing means comprises a magnet mounted on said flexible bladder and at least one Hall effect device mounted on said blood pumping chamber to detect the instantaneous displacement of said flexible bladder by detecting instantaneous changes in the position of said magnet, said Hall effect devices generating volume related signals as a function of time in accordance with the instantaneous changes in position of said magnet.

23. The control system of claim 22 wherein said programmed microprocessor means comprises a read only memory (ROM) and a central processing unit (CPU), wherein said read only memory is programmed with data which correlates the position signals from said Hall effect devices with the volume of blood in said blood pumping chambers as a function of time, said central processing unit being coupled to said read only memory to access the programmed data to determine the volume of blood in said blood pumping chamber.

24. The control system of claim 12 wherein said driving means comprises a brushless DC motor.

25. The control system of claim 24 wherein said control system further comprises means for commutating said brushless DC electric motor.

26. The control system of claim 25 wherein said means for commutating comprises a back-emf control circuit.

27. The control system of claim 26 wherein said programmed microprocessor means further comprises means for generating control signals which vary the speed of said motor.

28. The control system of claim 27 wherein said control system further comprises a digital to analog converter coupled to said microprocessor means to convert the control signals to analog signals, a speed control circuit coupled to said converter for generating speed control signals and a motor drive circuit responsive to the speed control signals to vary the speed of said electric motor.

29. The control system of claim 14 wherein said control system further comprises an analog to digital converter connected between said sensing means and said microprocessor means.

30. A control system according to claim 14 wherein said microprocessor means further comprises means for responding to the volume related signals to stop the ejection of blood from said blood pumping chamber when said blood pumping chamber is empty or when the systolic time period provided in accordance with the adjusted heart rate expires.

31. A control system according to claim 14 wherein said microprocessor means further comprises means for responding to the volume related signals to detect when said blood pumping chamber is full, said microprocessor means beginning ejection of blood from said blood pumping chamber when said blood pumping chamber is full or the diastolic time period provided by the adjusted heart rate expires.

32. The control system of claim 14 wherein said microprocessor means further comprises means for calculating the adjusted heart rate and the blood ejection rate so that the end diastolic volume of said blood pumping chamber equals the maximum ventricular volume and cardiac output equals venous return.

33. The control system of claim 14 wherein said microprocessor means further comprises means for determining the actual filling rate of said blood pumping chamber from the volume related signals, means for calculating the desired filling rate as a function of maximum ventricular volume and the diastolic time period, and means for determining the adjusted heart rate as a function of the difference between the desired filling rate and the actual filling rate.

34. The control system of claim 14 wherein said microprocessor means further comprises means for determining the actual ejection rate of said blood pumping chamber from the volume related signals, means for calculating the desired ejection rate as a function of the end diastolic volume and the systolic time period, and means for generating the control signals as a function of the difference between the desired ejection rate and the actual ejection rate.

35. The control system of claim 16 wherein said microprocessor means further comprises means for centering the systolic time period of said subordinate ventricle in the diastolic time period of said dominant ventricle, and vice versa.

36. In an implantable total cardiac prosthesis having dominant and subordinate ventricles which receive blood in response to body requirements and actuation means for ejecting blood from said dominant and subordinate ventricles, and electronic control system for controlling said actuation means, said electronic control system comprising:
 first sensing means adapted to be coupled to said dominant ventricle for determining the volume of blood in said dominant ventricle as a function of time;
 second sensing means adapted to be coupled to said subordinate ventricle for determining the volume of blood in said subordinate ventricle as a function of time;
 programmed microprocessor means coupled to said first sensing means for determining the filling flow rate of said dominant ventricle from the volume of blood in said dominant ventricle as a function of time and adjusting the heart rate at which said cardiac prosthesis fills and empties in response to the filling flow rate of said dominant ventricle to allow just enough time to said dominant ventricle to fill completely, said programmed microprocessor means further generating first control signals which adjust the blood ejection rate of said dominant ventricle in response to the adjusted heart rate, said programmed microprocessor means also being coupled to said second sensing means for generating second control signals which adjust the blood ejection rate of said subordinate ventricle in response to the adjusted heart rate and the volume of blood in said subordinate ventricle; and
 pump motor means coupled to said programmed microprocessor means for driving said actuation device, said pump motor means being responsive to the first and second control signals from said programmed microprocessor means to control said actuation device to eject blood from said dominant and subordinate ventricles in accordance with the adjusted blood ejection rates for each of said ventricles.

37. In an implantable total cardiac prosthesis having dominant and subordinate ventricles which receive blood in response to body requirements and actuation means for ejecting blood from said dominant and subordinate ventricles, an electronic control system for controlling said actuation means, said electronic control system comprising:
 first sensing means adapted to be coupled to said dominant ventricle for determining the volume of blood in said dominant ventricle as a function of time;
 second sensing means adapted to be coupled to said subordinate ventricle for determining the volume of blood in said subordinate ventricle as a function of time;
 control means coupled to said first and second sensing means for determining the filling flow rate of said dominant and subordinate ventricles from the volume of blood in said ventricles as a function of time, said control means including clock control means for adjusting the heart rate at which said cardiac prosthesis fills and empties in response to the filling flow rate of said dominant ventricle to allow just enough time for said dominant ventricle to fill completely, said control means further including first ejection rate control means for generating first control signals which adjust the blood ejection rate of said dominant ventricle in accordance with the adjusted heart rate and second ejection rate control means for generating second control signals which adjust the blood ejection rate of said subordinate ventricle in accordance with the adjusted heart rate and the instantaneous volume of blood in said subordinate ventricle; and
 pump motor means coupled to said control means for driving said actuation device, said pump motor means being responsive to the first and second control signals from said control means to control said actuation device to eject blood from said dominant and subordinate ventricles in accordance with the adjusted blood ejection rates for each of said ventricles.

38. An electronic control system for an implantable cardiac prosthesis having a blood pumping chamber and an actuation device for causing said blood pumping chamber to eject blood, said electronic control system commmprising:

sensing means adapted to be coupled to said blood pumping chamber for determining the volume of blood in said blood pumping chamber as a function of time;

control means coupled to said sensing means for generating control signals to control the actuation device, said control means including clock control means responsive to the volume of blood in said blood pumping chamber as a function of time for determining the filling flow rate of said blood pumping chamber and adjusting the heart rate at which said cardiac prosthesis fills and empties in response to the filling flow rate to allow just enough time for said blood pumping chamber to fill completely, said control means further including ejection rate control means for generating control signals which adjust the blood ejection rate of said blood pumping chamber as a function of the adjusted heart rate; and pump motor means coupled to said control means for driving said actuation device, said pump motor means being responsive to the control signals from said control means to control said actuation device to eject blood from said blood pumping chamber in accordance with the adjusted blood ejection rate for said blood pumping chamber.

39. A data processing system for controlling the operation of a cardiac prosthesis having two blood pumping chambers, one of which is the dominant blood pumping chamber, sensing means associated with each blood pumping chamber for generating volume signals related to the volume of blood in said blood pumping chambers as a function of time, actuation means for causing said blood pumping chambers to eject blood and pump motor means for driving said blood pumping chambers, said data processing system comprising:

input means connectable to said sensing means for receiving the volume related signals from said sensing means;

clock control means coupled to said input means for determining the filling flow rates of said blood pumping chambers in response to the volume related signals and adjusting the heart rate at which said cardiac prosthesis fills and empties in response to the filling flow rate of said dominant blood pumping chamber to allow just enough time for said dominant blood pumping chamber to fill to a predetermined volume;

ejection rate control means for each of said blood pumping chambers, said ejection rate control means being cupled to said clock control means for generating control signals which adjust the blood ejection rates of said blood pumping chambers in accordance with the adjusted heart rate and the volume related signals so that the cardiac output of said cardiac prosthesis equals the venous return during each heart rate cycle; andd output means coupled to said ejection rate control means for outputting the control signals to said pump motor means.

40. In an implantable total cardiac prosthesis having dominant and subordinate ventricles which receive blood in response to body requirements, an actuation device for ejecting blood from said dominant and subordinate ventricles and pump motor means for driving said actuation device, a method of operating an electronic control system comprising the steps of:

sensing the volume of blood in said dominant and subordinate ventricles as a function of time and generating volume related signals representative of the volume as a function of time;

determining the filling flow rates of said ventricles from the volume related signals;

adjusting the heart rate at which said cardiac prosthesis fills and empties as a function of the filling flow rate of said dominant ventricle to allow just enough time for said dominant ventricle to fill to a predetermined volume;

generating first control signals which adjust the ejection rate of said dominant ventricle in accordance with the adjusted heart rate;

generating second control signals which adjust the ejection rate of said subordinate ventricle in accordance with the adjusted heart rate and volume related signals from said subordinate ventricles; and controlling said pump motor means and said actuation means with the first and second control signals to thereby control the ejection rates of said dominant and subordinate ventricles, respectively.

41. A method of operating a total cardiac prosthesis with the aid of a microcomputer, said cardiac prosthesis having dominant and subordinate ventricles, actuation means for causing said ventricles to eject blood and pump motor means for driving said actuation means, the method comprising the steps of:

providing said microcomputer with volume information on the volume of blood in said dominant and subordinate ventricles as a function of time;

determining the actual filling flow rates of said dominant and subordinate ventricles from the volume information;

repetitively adjusting the heart rate of said cardiac prosthesis as a function of the actual filling flow rate of said dominant ventricle so that the volume of said dominant ventricle after diastole equals the maximum capacity of said dominant ventricle;

repetitively calculating the desired ejection rates of said dominant and subordinate ventricles in accordance with the adjusted heart rate and the volume information so that cardiac output can equal venous return and cardiac output occurs within the systolic time period allowed by the adjusted heart rate;

repetitively generating control signals for said pump motor means in accordance with the calculated ejection rates; and outputting the control signals to said pump motor means to drive said actuation means to eject blood from said dominant and subordinate ventricles at ejection rates corresponding to the calculated ejection rates.

* * * * *